(12) United States Patent
Zhang et al.

(10) Patent No.: US 12,215,390 B2
(45) Date of Patent: Feb. 4, 2025

(54) INTEGRATION OF TUMOR CHARACTERISTICS WITH BREAST CANCER INDEX

(71) Applicant: BIOTHERANOSTICS, INC., San Diego, CA (US)

(72) Inventors: Yi Zhang, San Diego, CA (US); Catherine A. Schnabel, San Diego, CA (US)

(73) Assignee: BIOTHERANOSTICS, INC., San Diego, CA (US)

( * ) Notice: Subject to any disclaimer, the term of this patent is extended or adjusted under 35 U.S.C. 154(b) by 69 days.

(21) Appl. No.: 18/056,967

(22) Filed: Nov. 18, 2022

(65) Prior Publication Data

US 2023/0083179 A1 Mar. 16, 2023

Related U.S. Application Data

(62) Division of application No. 15/349,915, filed on Nov. 11, 2016, now Pat. No. 11,530,448.

(60) Provisional application No. 62/265,964, filed on Dec. 10, 2015, provisional application No. 62/255,260, filed on Nov. 13, 2015.

(51) Int. Cl.
| | | |
|---|---|---|
| *C12Q 1/6886* | (2018.01) | |
| *A61K 31/337* | (2006.01) | |
| *A61K 31/513* | (2006.01) | |
| *A61K 31/675* | (2006.01) | |
| *A61K 31/704* | (2006.01) | |
| *A61K 45/06* | (2006.01) | |

(52) U.S. Cl.
CPC .......... *C12Q 1/6886* (2013.01); *A61K 31/337* (2013.01); *A61K 31/513* (2013.01); *A61K 31/675* (2013.01); *A61K 31/704* (2013.01); *A61K 45/06* (2013.01); *C12Q 2600/106* (2013.01); *C12Q 2600/118* (2013.01); *C12Q 2600/158* (2013.01)

(58) Field of Classification Search
CPC ............ C12Q 1/6886; C12Q 2600/106; C12Q 2600/118; C12Q 2600/158; A61K 31/337
See application file for complete search history.

(56) References Cited

U.S. PATENT DOCUMENTS

| | | |
|---|---|---|
| 4,981,783 A | 1/1991 | Augenlicht |
| 6,291,170 B1 | 9/2001 | Van Gelder et al. |
| 6,328,709 B1 | 12/2001 | Hung et al. |
| 6,482,600 B1 | 11/2002 | Burner et al. |
| 6,642,009 B2 | 11/2003 | Hung |
| 6,673,024 B2 | 1/2004 | Soito et al. |
| 6,794,141 B2 | 9/2004 | Erlander et al. |
| 7,504,214 B2 | 3/2009 | Erlander et al. |
| 7,514,209 B2 | 4/2009 | Dai et al. |
| 7,930,105 B2 | 4/2011 | Erlander et al. |
| 9,447,470 B2 | 9/2016 | Erlander et al. |
| 2001/0039015 A1 | 11/2001 | Sauter |
| 2002/0044941 A1 | 4/2002 | Rosen et al. |
| 2002/0102265 A1 | 8/2002 | Hong et al. |
| 2003/0049701 A1 | 3/2003 | Muraca |
| 2003/0087270 A1 | 5/2003 | Schlegel et al. |
| 2003/0124128 A1 | 7/2003 | Lillie et al. |
| 2003/0138833 A1 | 7/2003 | Polyak et al. |
| 2003/0219760 A1 | 11/2003 | Gordon et al. |
| 2005/0079518 A1 | 4/2005 | Baker et al. |
| 2005/0239079 A1 | 10/2005 | Erlander et al. |
| 2005/0239083 A1 | 10/2005 | Erlander et al. |
| 2006/0154267 A1 | 7/2006 | Ma et al. |
| 2011/0136680 A1 | 6/2011 | Erlander et al. |
| 2013/0281502 A1 | 10/2013 | Sgroi et al. |
| 2015/0072021 A1 | 3/2015 | Cheang et al. |
| 2015/0203921 A1 | 7/2015 | Schnabel et al. |
| 2015/0344967 A1 | 12/2015 | Schnabel et al. |
| 2017/0073767 A1 | 3/2017 | Ma et al. |

FOREIGN PATENT DOCUMENTS

| | | |
|---|---|---|
| EP | 2333119 A1 | 6/2011 |
| WO | WO 2002/103320 A2 | 12/2002 |
| WO | WO 2003/060470 A2 | 7/2003 |
| WO | WO 2005/008213 A2 | 1/2005 |
| WO | WO 2006/004600 A1 | 1/2006 |
| WO | WO 2006/119593 A1 | 11/2006 |
| WO | WO 2006/132971 A2 | 12/2006 |
| WO | WO 2009/108215 A1 | 9/2009 |
| WO | WO 2012/079059 A2 | 6/2012 |
| WO | WO 2012/079059 A3 | 6/2012 |
| WO | WO 2013/070521 A1 | 5/2013 |
| WO | WO 2015/038682 A1 | 3/2015 |
| WO | WO 2015/184182 A1 | 12/2015 |

OTHER PUBLICATIONS

Gyorffy et al., "Multigene prognostic tests in breast cancer: past, present, future," Breast Canc. Res., 17:11 (2015).
Jerevall et al., "Prognostic utility of HOXB 13:IL17BR and molecular grade index in early-stage breast cancer patients from the Stockholm trial," Br. J. Cancer, 104:1762-1769 (2011).
Rakha et al., "Nottingham prognostic index plus (NPI+): a modern clinical decision making tool in breast cancer," Br. J. Cancer, 110(7):1688-1697 (2014).
Sestak et al., "Integration of tumor size and grade with the breast cancer index (BCI) for prediction of distant recurrence in hormone receptor-positive breast cancer with 1-3 positive lymph nodes," Cancer Res., Abstract P2-08-12 (2016).
Fan et al., "Fan et al. (BMC Medical Genomics 2011, 4:3, 1-15," BMC Medical Genomics, 4(3):1-15 (2011).

(Continued)

*Primary Examiner* — Sarae L Bausch
(74) *Attorney, Agent, or Firm* — Finnegan, Henderson, Farabow, Garrett & Dunner, LLP; Michael J. Gilly

(57) ABSTRACT

Methods of determining risk of recurrence of a breast cancer of a subject are provided. Also provided are methods of predicting responsiveness to a therapy of a breast cancer of a subject. Additionally, methods of recommending treatment for a subject that has breast cancer are provided. Further provided are methods of treating a subject that has breast cancer. Systems for performing described methods are also provided.

20 Claims, 8 Drawing Sheets

(56) References Cited

OTHER PUBLICATIONS

Abramovitz et al., "A systems approach to clinical oncology: focus on breast cancer," *Proteome Sci.*, 4:5 (2006).
Alizadeh et al., "Distinct types of diffuse large B-cell lymphoma identified by gene expression profiling," *Nature*, 403(6769):503-511 (2000).
Ansfield et al., "A ten-year study of 5-flurouracil in disseminated breast cancer with clinical results and survival times," *Cancer Res.*, 29(5):1062-1066 (1969).
Arama et al., "Murine NIMA-related kinases are expressed in patterns suggesting distinct functions in gametogenesis and a role in the nervous system," *Oncogene*, 16:1813-1823 (1998).
Bardou et al., "Progesterone receptor status significantly improves outcome prediction over estrogen receptor status alone for adjuvant endocrine therapy in two large breast cancer databases," *J. Clin. Oncol.*, 21(10):1973-1979 (2003).
Becker et al., "Distinct gene expression patterns in a tamoxifen-sensitive human mammary carcinoma xenograft and its tamoxifen-resistant subline MaCa 3366/TAM," *Mal. Cancer Ther.*, 4(1):151-168 (2005).
Benner et al., "Evolution, language and analogy in functional genomics," *TRENDS Genetics*, 17(7):414-418 (2001).
Bepler et al., "RRM1 and PTEN as prognostic parameters for overall and disease-free survival in patients with non-small-cell lung cancer," *J. Clin. Oncol.*, 22(10):1878-1885 (2004).
Betsil et al., "Intraductal carcinoma. Long-term follow-up after treatment by biopsy alone," *JAMA*, 239(18):1863-1867 (1978).
BIG 1-98 Collaborative Group et al., "Letrozole therapy alone or in sequence with tamoxifen in women with breast cancer," *N. Engl. J. Med.*, 361(8):766-776 (2009).
Bissett et al., "Human papillomavirus genotype detection and viral load in paired genital and urine samples from both females and males," *J. Med. Viral.*, 83:1744-1751 (2011).
Bittner et al., "Molecular classification of cutaneous malignant melanoma by gene expression profiling," *Nature*, 406(6795):536-540 (2000).
Bonner et al., "Laser capture microdissection: molecular analysis of tissue," *Science*, 278(5342):1481-1483 (1997).
Brown et al., "Knowledge based analysis of microarray gene expression data by using support vector machines," *Proc. Natl. Acad. Sci. USA*, 97(1):262-267 (2000).
Bruggemeier et al., "Aromatase inhibitors in the treatment of breast cancer," *Endocrine Rev.*, 26(3):331-345 (2005).
Buzdar, "Anastrozole: a new addition to the armamentarium against advanced breast cancer," Am. *J. Clin. Oncol.*, 21(2):161-166 (1998).
Chen et al., "BRCA1, BRCA2, and Rad51 operate in a common DNA damage response pathway," *Cancer Res.*, 59(7 Suppl): 1752s-1756s (1999).
Chen et al., "Discordant protein and mRNA expression in lung adenocarcinomas," *Mal. Cell. Proteomics*, 1:304-313 (2002).
Chen et al., "Inhibition of human cancer cell growth by inducible expression of human ribonucleotide reductase antisense cDNA," *Antisense Nucleic Acid Drug Dev.*, 10(2):111-116 (2000).
Chng et al., "A gene expression based centrosome index is a powerful prognostic factor in myeloma," *Blood*, 108; Abstract 3388 (2006).
Cianfrocca et al., "Prognostic and predictive factors in early-stage breast cancer," *Oncologist*, 9(6):606-616 (2004).
Clarke et al., "Antiestrogen resistance in breast cancer and the role of estrogen receptor signaling," *Oncogene*, 22:7316-7339 (2003).
Collins et al., "The application of genomic and proteomic technologies in predictive, preventive and personalized medicine," *Vascul. Pharmacol.*, 45(5):258-267 (2006).
Cornfield et al., "The prognostic significance of multiple morphologic features and biologic markers in ductal carcinoma in situ of the breast: a study of a large cohort of patients treated with surgery alone," *Cancer*, 100(11):2317-2327 (2004).

Cronin et al., "Measurement of gene expression in archival paraffin-embedded tissues: development and performance of a 92-gene reverse transcriptase-polymerase chain reaction assay," *Am. J. Pathol.*, 164(1):35-42 (2004).
Cuzick et al., "Effect of anastrozole and tamoxifen as adjuvant treatment for early-stage breast cancer; 10-year analysis of the ATAC trial," *Lancet Oncol.*, 11:1135-1142 (2010).
Cuzick et al., "Prognostic value of a cominded estrogen receptor, progesterone receptor, Ki-67, and human epidermal growth factor receptor 2 immunohistochemical score and comparison with the genomic health recurrence score in early breast cancer," *J. Clin. Oncol.*, 29(32):4273-4278 (2011).
Dabholkar et al., "Messenger RNA levels of XPAC and ERCCI in ovarian cancer tissue correlate with response to platinum-based chemotherapy," *J. Clin. Invest.*, 94:703-708 (1994).
Daidone et al., "Biomarkers and outcome after tamoxifen treatment in node-positive breast cancers from elderly women," *Br. J. Cancer*, 82(2):270-277 (2000).
Dalgin et al., "Portraits of breast cancer progression," *BMC Bioinformatics*, 8(291):1-16 (2007).
Dalton et al., "Histologic grading of breast cancer: linkage of patient outcome with level of pathologist agreement," *Mod. Pathol.*, 13(7):730-735 (2000).
Dauvois et al., "Antiestrogen ICI 164,384 reduces cellular estrogen receptor content by increasing its turnover," *Proc. Natl. Acad. Sci. USA*, 89:4037-4041 (1992).
De Vos et al., "Gene expression profile of serial samples of transformed B-cell lymphomas," *Lab. Invest.*, 83(2):271-285 (2003).
Derisi et al., "Use of a cDNA microarray to analyse gene expression patterns in human cancer," *Nat. Genet.*, 14(4):457-460 (1996).
Desmedt et al., "Proliferation: the most prominent predictor of clinical outcome in breast cancer," *Cell Cycle*, 5(19):2198-2202 (2006).
Desmedt et al., "Strong time dependence of the 76-gene prognostic signature for node-negative breast cancer patients in the TRANSBIG multicenter independent validation series," *Clin. Cancer Res.*, 13(11):3207-3214 (2007).
Dowsett et al., "Prediction of risk of distant recurrence using the 21-gene recurrence score in node-negative and node-positive postmenopausal patients with breast cancer treated with anastrozole or tamoxifen; a transATAC study," *J. Clin. Oncol.*, 28(11):1829-1834 (2010).
Dowsett, "Overexpression of HER-2 as a resistance mechanism to hormonal therapy for breast cancer," *Endocr. Relat. Cancer*, 8(3):191-195 (2001).
Draghici et al., "A systems biology approach for pathway level analysis," *Genome Res.*, 17:1537-1545 (2007).
Dupont et al., "Risk factors for breast cancer in women with proliferative breast disease," *N. Engl. J. Med.*, 312(3):146-151 (1985).
Dutertre et al., "Molecular mechanisms of selective estrogen receptor modulator (SERM) action," *J. Pharmacol. Exper. Ther.*, 295(2):431-437 (2000).
Ellis et al., "Letrozole is more effective neoadjuvant endocrine therapy than tamoxifen for ErbB-1- and/or ErbB-2-positive, estrogen receptor-positive primary breast cancer: evidence from a phase III randomized trial," *J. Clin. Oncol.*, 19(18):3808-3816 (2001).
Ellis et al., "Neoadjuvant comparisons of aromatase inhibitors and tamoxifen: pretreatment determinants of response and on-treatment effect," *J. Steroid Biochem. Mal. Biol.*, 86:301-307 (2003).
Elston et al., "Pathological prognostic factors in breast cancer. I. The value of histological grade in breast cancer: experience from a large study with long-term follow-up," *Histopathology*, 19(5):403-410 (1991).
Ester et al., "Impaired BUB1B mRNA expression is associated with osteogenic sarcoma," *Proc. Am. Assoc. Cancer Res.*, 46:1052, Abstract 4448 (2005).
Fabian et al., "Short-term breast cancer prediction by random periareolar fine-needle aspiration cytology and the gail risk model," *J. Natl. Cancer Inst.*, 92(15):1217-1227 (2000).
Feng et al., "Molecular biomarkers for cancer detection in blood and bodily fluids," *Crit. Rev. Clin. Lab. Sci.*, 43(5-6):497-560 (2006).

(56) References Cited

OTHER PUBLICATIONS

Fernandez et al., "Quantitative oestrogen and progesterone receptor values in primary breast cancer and predictability of response to endocrine therapy," *Clin. Oncol.*, 9:245-250 (1983).
Fernö et al., "Results of two or five years of adjuvant tamoxifen correlated to steroid receptor and S-phase levels," *Breast Cancer Res. Treat.*, 59:69-76 (2000).
Filipits et al., "A new molecular predictor of distant recurrence in ER-positive, HER2-negative breast cancer adds independent information to conventional clinical risk factors," *Clin. Cancer Res.*, 17:6012-6020 (2011).
Fitzgibbons et al., "Prognostic factors in breast cancer. College of American Pathologists Consensus Statement 1999," *Arch. Pathol. Lab. Med.*, 124(7):966-978 (2000).
Fraser et al., "Columnar alteration with prominent apical snouts and secretions: a spectrum of changes frequently present in breast biopsies performed for microcalcifications," *Am. J. Surg. Pathol.*, 22(12):1521-1527 (1998).
Furey et al., "Support vector machine classification and validation of cancer tissue samples using microarray expression data," *Bioinformatics*, 16(10):906-914 (2000).
Galaktionov et al., "CDC25 phosphatases as potential human oncogenes," *Science*, 269(5230):1575-1577 (1995).
Garber et al., "Diversity of gene expression in adenocarcinoma of the lung," *Proc. Natl. Acad. Sci. USA*, 98(24):13784-13789 (2001).
Gelmini et al., "Quantitative polymerase chain reaction-based homogeneous assay with fluorogenic probes to measure c-erbB-2 oncogene amplification," *Clin. Chem.*, 43(5):752-758 (1997).
GENBANK Accession No. AA454563.1, Jun. 6, 1997.
Gianni et al., "Feasibility and tolerability of sequential doxorubicin/paclitaxel followed by cyclophosphamide, methotrexate, and fluorouracil and its effects on tumor response as preoperative therapy," *Clin. Cancer Res.*, 11(24 Pt 1):8715-8721 (2005).
Gibson et al., "A novel method for real time quantitative RT-PCR," *Genome Res.*, 6:995-1001 (1996).
Ginzinger, "Gene quantification using real-time quantitative PCR: an emerging technology hits the mainstream," *Exp. Hematol.*, 30:503-512 (2002).
Goetz et al., "A two-gene expression ratio of homeobox 13 and interleukin-17B receptor for prediction of recurrence and survival in women receiving adjuvant tamoxifen," *Clin. Cancer Res.*, 12(7 Pt 1):2080-2087 (2006).
Goldhirsch et al., "Meeting highlights: international expert consensus on the primary therapy of early breast cancer 2005," *Ann. Oncol.*, 16(10):1569-1583 (2005).
Golpon et al., "HOX genes in human lung. Altered expression in primary pulmonary hypertension and emphysema," *Am. J. Pathol.*, 158(3):955-966 (2001).
Golub et al., "Molecular classification of cancer: class discovery and class prediction by gene expression monitoring," *Science*, 286(5439):531-537 (1999).
Gonzalez-Angulo et al. "Future of personalized medicine in oncology: a systems biology approach," *J. Clin. Oncol.*, 28(16):2777-2783 (2010).
Goss et al., "A randomized trial of letrozole in postmenopausal women after five years of tamoxifen therapy for early-stage breast cancer," *N. Engl. J. Med.*, 349(19):1793-1802 (2003).
Goss et al., "Randomized Trial of Letrozole Following Tamoxifen as Extended Adjuvant Therapy in Receptor-Positive Breast Cancer: Updated Findings from NCIC CTG MA 17," *J. Natl. Cancer Inst.*, 97(17):1262-1271 (2005).
Gruvberger et al., "Estrogen receptor status in breast cancer is associated with remarkably distinct gene expression patterns," *Cancer Res.*, 61(16):5979-5984 (2001).
Habel et al., "HOXB13:IL17BR and molecular grade index and risk of breast cancer death among patients with lymph node-negative invasive disease," *Breast Cancer Res.*, 15:R24 (2013).
Hall et al., "The multifaceted mechanisms of estradiol and estrogen receptor signaling," *J. Biol. Chem.*, 276(40):36869-36872 (2001).
Hartmann et al., "Benign breast disease and the risk of breast cancer," *N. Engl. J. Med.*, 353(3):229-237 (2005).
Hedenfalk et al., "Gene-expression profiles in hereditary breast cancer," *N. Engl. J. Med.*, 344(8):539-548 (2001).
Herschkowitz et al., "Identification of conserved gene expression features between murine mammary carcinoma models and human breast tumors," *Genome Biol.*, 8:R76 (2007).
Hilsenbeck et al., "Statistical analysis of array expression data as applied to the problem of tamoxifen resistance," *J. Natl. Cancer Inst.*, 91(5):453-459 (1999).
Hirose et al., "MgcRacGAP is involved in cytokinesis through associating with mitotic spindle and midbody," *J. Biol. Chem.*, 276(8):5821-5828 (2001).
Holland et al., "Ductal carcinoma in situ: a proposal for a new classification," *Semin. Diagn. Pathol.*, 11(3):167-180 (1994).
Howell et al., "Where do selective estrogen receptor modulators (SERMs) and aromatase inhibitors (AIs) now fit into breast cancer treatment algorithms?," *J. Steroid Biochem. Mol. Biol.*, 79(1-5):227-237 (2001).
Howell et al., "The use of selective estrogen receptor modulators and selective estrogen receptor down-regulators in breast cancer," *Best Pract. Res. Clin. Endocrinol Metab.*, 18(1):47-66 (2004).
Huang et al., "Gene expression predictors of breast cancer outcomes," *Lancet*, 361:1590-1596 (2003).
Ivshina et al., "Genetic reclassification of histologic grade delineates new clinical subtypes of breast cancer," *Cancer Res.*, 66(21):10292-10301 (2006).
Jansen et al., "HOXB13-to-IL17BR expression ratio is related with tumor aggressiveness and response to tamoxifen of recurrent breast cancer: a retrospective study," *J. Clin. Oncol.*, 25(6):662-668 (2007).
Jerevall et al., "Exploring the two-gene ratio in breast cancer-independent roles for HOXB13 and IL17BR in prediction of clinical outcome," *Breast Cancer Res. Treat.*, 107(2):225-234 (2008).
Jerevall et al., "Predictive relevance of HOXB13 protein expression for tamoxifen benefit in breast cancer," *Breast Cancer Res.*, 12(4):R53 (2010).
Jordan et al., "Historical perspective on hormonal therapy of advanced breast cancer," *Clin. Ther.*, 24(Suppl. A):A3-A16 (2002).
Jordan et al., "Introducing a new section to breast cancer research: endocrinology and hormone therapy," *Breast Cancer Res.*, 5:281-283 (2003).
Kato et al., "Expression of survivin in esophageal cancer: correlation with the prognosis and response to chemotherapy," *Int. J. Cancer (Pred. Oncol.)*, 95:92-95 (2001).
Korkaya et al., "Regulation of mammary stem/progenitor cells by PTEN/Akt/β-catenin signaling," *PloS Biology*, 7(6):e100121 (2009).
Lennon et al., "The I.M.A.G.E. Consortium: an integrated molecular analysis of genomes and their expression," *Genomics*, 33(1):151-152 (1996).
Levenson et al., "Gene expression profiles with activation of the estrogen receptor α-selective estrogen receptor modulator complex in breast cancer cells expressing wild-type estrogen receptor," *Cancer Res.*, 62:4419-4426 (2002).
Lewis et al., "Molecular classification of melanoma using real-time quantitative reverse transcriptase-polymerase chain reaction," *Cancer*, 104(8):1678-1686 (2005).
Lingle et al., "Centrosome amplification drives chromosomal instability in breast tumor development," *Proc. Natl. Acad. Sci. USA*, 99(4):1978-1983 (2002).
Loi et al., "Definition of clinically distinct molecular subtypes in estrogen receptor-positive breast carcinomas through genomic grade," *J. Clin. Oncol.*, 25(10):1239-1246 (2007).
Lu et al., "Selection of potential markers for epithelial ovarian cancer with gene expression arrays and recursive descent partition analysis," *Clin. Cancer Res.*, 10:3291-3300 (2004).
Lucentini et al., "Gene association studies typically wrong," *The Scientist*, 18(24):20 (2004).
Luo et al., "Gene expression profiles of laser-captured adjacent neuronal subtypes," *Nat. Med.*, 5(1):117-122 (1999).
Luo et al., "Higher expression of human kallikrein 10 in breast cancer tissue predicts tamoxifen resistance," *Br. J. Cancer*, 86:1790-1796 (2002).

(56) References Cited

OTHER PUBLICATIONS

Ma et al., "A five-gene molecular grade index and HOXB13:IL17BR are complementary prognostic factors in early stage breast cancer," *Clin. Cancer Res.*, 14(9):2601-2608 (2008).

Ma et al., "A two-gene expression ratio predicts clinical outcome in breast cancer patients treated with tamoxifen," *Cancer Cell.*, 5(6):607-616 (2004).

Ma et al., "Gene expression profiles of human breast cancer progression," *Proc. Natl. Acad. Sci. USA*, 100(10):5974-5979 (2003).

Ma et al., "HOXB13 may predict response to neoadjuvant letrozole in patients with estrogen receptor-positive breast cancer," Novartis poster, retrieved from the Internet. URL:http://www.biotheranostics.com/wp-content/uploads/Novartis-BTX_SABCS_2009.pdf, retrieved on Dec. 17, 2014, Abstract only.

Ma et al., "The HOXB13:IL17BR expression index is a prognostic factor in early-stage breast cancer," *J. Clin. Oncol.*, 24(28):4611-4619 (2006).

Maacke et al., "Over-expression of wild-type Rad5 I correlates with histological grading of invasive ductal breast cancer," *Int. J. Cancer*, 88(6):907-913 (2000).

Mark et al., "HER-2/neu gene amplification in stages I-IV breast cancer detected by fluorescent in situ hybridization," *Genet. Med.*, 1(3):98-103 (1999).

Marshall et al., "Risk of breast cancer associated with atypical hyperplasia of lobular and ductal types," *Cancer Epidemiol Biomarkers Prev.*, 6(5):297-301 (1997).

May, "How many species are there on earth?," *Science*, 241:1441-1449 (1988).

Mello-Grand et al., "Gene expression profiling and prediction of response to hormonal neoadjuvant treatment with anastrozole in surgically resectable breast cancer," *Breast Cancer Res. Treat.*, 121:399-411 (2010).

Miller et al., "An expression signature for p53 status in human breast cancer predicts mutation status, transcriptional effects, and patient survival," *Proc. Natl. Acad. Sci. USA*, 102(38):13550-13555 (2005).

Miller et al., "Gene expression profiles differentiating between breast cancers clinically responsive or resistant to letrozole," *J. Clin. Oncol.*, 27(9):1382-1387 (2009).

Nardelli et al., "Estrogen and progesterone receptors status in the prediction of response of breast cancer to endocrine therapy," *Eur. J. Gynaec. Oncol.*, 3:151-158 (1986).

Nicholson et al., "Epidermal growth factor receptor in breast cancer: association with response to endocrine therapy," *Breast Cancer Res. Treat.*, 29:117-125 (1994).

O'Driscoll et al., "Multiple drug resistance-related messenger RNA expression in archival formalin-fixed paraffin-embedded human breast tumour tissue," *Eur. J. Cancer*, 32A(1):128-133 (1996).

Okuda et al., "Epigenetic inactivation of the candidate tumor suppressor gene HOXB13 in human renal cell carcinoma," *Oncogene*, 25:1733-1742 (2006).

Osborne et al., "Growth factor receptor cross-talk with estrogen receptor as a mechanism for tamoxifen resistance in breast cancer," *The Breast*, 12:362-367 (2003).

Osborne et al., "The value of estrogen and progesterone receptors in the treatment of breast cancer," *Cancer*, 46:2884-2888 (1980).

Oyama et al., "Atypical cystic lobules: an early stage in the formation of low-grade ductal carcinoma in situ," *Virchows Arch.*, 435(4):413-421 (1999).

Page et al., "Combined histologic and cytologic criteria for the diagnosis of mammary atypical ductal hyperplasia," *Hum. Pathol.*, 23(10):1095-1097 (1992).

Page et al., "Intraductal carcinoma of the breast: follow-up after biopsy only," *Cancer*, 49(4):751-758 (1982).

Page et al., "Prediction of node-negative breast cancer outcome by histologic grading and S-phase analysis by flow cytometry: an Eastern Cooperative Oncology Group Study (2192)," *Am. J. Clin. Oncol.*, 24(1):10-18 (2001).

Paik et al., "A multigene assay to predict recurrence of tamoxifen-treated, node-negative breast cancer," *N. Engl. J. Med.*, 351(27):2817-2826 (2004).

Paik, "Molecular profiling of breast cancer," *Breast Cancer*, 18:59-63 (2006).

Pawitan et al., "Gene expression profiling spares early breast cancer patients from adjuvant therapy: derived and validated in two population-based cohorts," *Breast Cancer Res.*, 7(6):R953-R964 (2005).

Pepe et al., "An interpretation for the ROC curve and inference using GLM procedures," *Biometrics*, 56(2):352-359 (2000).

Perou et al., "Distinctive gene expression patterns in human mammary epithelial cells and breast cancers," *Proc. Natl. Acad. Sci. USA*, 96(16):9212-9217 (1999).

Perou et al., "Molecular portraits of human breast tumours," *Nature*, 406(6797):747-752 (2000).

Ramaswamy et al., "A molecular signature of metastasis in primary solid tumors," *Nat. Genet.*, 33(1):49-54 (2003).

Romond et al., "Trastuzumab plus adjuvant chemotherapy for operable HER2-positive breast cancer," *N. Engl. J. Med.*, 353(16):1673-1684 (2005).

Rundle et al., "Design options for molecular epidemiology research within cohort studies," *Cancer Epidemiol Biomarkers Prev.*, 14(8)1899-1907 (2005).

Saito-Hisaminato et al., "Genome-wide profiling of gene expression in 29 normal human tissues with a cDNA microarray," *DNA Res.*, 9:35-45 (2002).

Salonga et al., "Colorectal tumors responding to 5-fluororacil have low gene expression levels of dihydropyrimidine dehydrogenase, thymidylate synthase, and thymidine phosphorylase," *Clin. Cancer Res.*, 6:1322-1327 (2000).

Scintu et al., "Genomic instability and increased expression of BUB1B and MAD2L1 genes in ductal breast carcinoma," *Cancer Letters*, 254:298-307 (2007).

Sengar et al., "The EH and SH3 domain Ese proteins regulate endocytosis by linking to dynamin and Eps15," *EMBO J.*, 18(4):1159-1171 (1999).

Sgroi et al., "In vivo gene expression profile analysis of human breast cancer progression," *Cancer Res.*, 59(22):5656-5661 (1999).

Sgroi et al., "Prediction of late disease recurrence and extended adjuvant letrozole benefit by the HOXB13/IL17BR biomarker," *JNCI*, 105(14):1036-1042 (2013).

Sgroi et al., "Prediction of late distant recurrence in patients with oestrogen-receptor-positive breast cancer: a prospective comparison of the breast-cancer index (BCI) assay, 21-gene recurrence score, and IHC4 in the TransATAC study population," *Lancet Oncol.*, 14:1067-1076 (2013).

Shah et al., "HOXB13 mediates tamoxifen resistance and invasiveness in human breast cancer by suppressing ERα and inducing IL-6 expression," *Cancer Res.*, 73(17):5449-5458 (2013).

Sheridan et al., "Control of TRAIL-induced apoptosis by a family of signaling and decoy receptors," *Science*, 277(5327):818-821 (1997).

Shi et al., "A novel cytokine receptor-ligand pair," *J. Biol. Chem.*, 2;75(25):19167-19176 (2000).

Shou et al., "Mechanisms of tamoxifen resistance: increased estrogen receptor-HER2/neu cross-talk in ER/HER2-positive breast cancer," *J. Natl. Cancer Inst.*, 96(12):926-935 (2004).

Singletary et al., "Revision of the American joint committee on cancer staging system for breast cancer," *J. Clin. Oncol.*, 20(17):3628-3636 (2002).

Sørlie et al., "Gene expression patterns of breast carcinomas distinguish tumor subclasses with clinical implications," *Proc. Natl. Acad. Sci. USA*, 98(19):10869-10874 (2001).

Sørlie et al., "Repeated observation of breast tumor subtypes in independent gene expression data sets," *Proc. Natl. Acad. Sci. USA*, 100(14):8418-8423 (2003).

Sotiriou et al., "Breast cancer classification and prognosis based on gene expression profiles from a population-based study," *Proc. Natl. Acad. Sci. USA*, 100(18):10393-10398 (2003).

Sotiriou et al., "Gene expression profiles derived from fine needle aspiration correlate with response to systemic chemotherapy in breast cancer," *Breast Cancer Res.*, 4:R3 (2002).

(56) References Cited

OTHER PUBLICATIONS

Sotiriou et al., "Gene expression profiling in breast cancer: understanding the molecular basis of histologic grade to improve prognosis," *J. Nat. Cancer Inst.*, 98(4):262-272 (2006).
Sotiriou et al., "Gene expression profiling in breast cancer: understanding the molecular basis of histologic grade to improve prognosis," *J. Nat. Cancer Inst.*, 98(4) Supplemental Data (2006).
Sotiriou et al., "Taking gene-expression profiling to the clinic: when will molecular signatures become relevant to patient care?," *Nat. Rev. Cancer*, 7(7):545-553 (2007).
Srinivas et al., "Trends in biomarker research for cancer detection," *Lancet Oncol.*, 2:698-704 (2001).
Strauss et al., "Detection and typing of human papillomavirus DNA in paired urine and cervical scrapes," *Eur. J. Epidermiol*, 15(6):537-543 (1999).
Tan-Chiu et al., "Effects of tamoxifen on benign breast disease in women at high risk for breast cancer," *J. Natl. Cancer Inst.*, 95(4):302-307 (2003).
Tarca et al., "A novel signaling pathway impact analysis," *Bioinformatics*, 25:75-82 (2009).
Thomas et al., "The Elf group of Ets-related transcription factors ELF3 and ELF5," *Adv. Exper. Med Biol.*, 480:123-128 (2000).
Turner et al., "Adjuvant chemotherapy: Which patient? What regimen?," ASCO University, 2013 ASCO Educational Book, [Retrieved on Aug. 17, 2015]. Online eBook. Retrieved from the Internet: <URL:http://meetinglibrary.asco.org/contenU145-132> 5 pages (2013).
Unger et al., "Characterization of adjacent breast tumors using oligonucleotide microarrays," *Breast Cancer Res.*, 3(5):336-341 (2001).
Van De Vijver et al., "A gene-expression signature as a predictor of survival in breast cancer," *N. Engl. J. Med*, 347:1999-2009 (2002).
Van Der Flier et al., "Bcar1/p130Cas protein and primary breast cancer: prognosis and response to tamoxifen treatment," *J. Natl. Cancer Inst.*, 92(2):120-127 (2000).
Van Rijnsoever et al., "Characterisation of colorectal cancers showing hypermethylation at multiple CpG islands," *Gut*, 51(6):797-802 (2002).
Van Slooten et al., "Expression of Bcl-2 in node-negative breast cancer is associated with various prognostic factors, but does not predict response to one course of perioperative chemotherapy," *Br. J. Cancer*, 74(1):78-85 (1996).
Van't Veer et al., "Gene expression profiling predicts clinical outcome of breast cancer," *Nature*, 415(6871):530-536 (2002).
Wang et al., "Gene-expression profiles to predict distant metastasis of lymph-node-negative primary breast cancer," *Lancet*, 365(9460):671-679 (2005).
West et al., "Predicting the clinical status of human breast cancer by using gene expression profiles," *Proc. Natl. Acad. Sci. USA*, 98(20):11462-11467 (2001).
Whitfield et al., "Identification of genes periodically expressed in the human cell cycle and their expression in tumors," *Mal. Biol. Cell.*, 13(6):1977-2000 (2002).
Wickerham, "Tamoxifen—an update on current data and where it can now be used," *Breast Cancer Res. Treat.*, 75:S7-S12 (2002).
Wijayarante et al., "Comparative analyses of mechanistic differences among antiestrogens," *Endocrinol.*, 140(12):5828-5840 (1999).
Willson et al., "Dissection of the molecular mechanism of action of GW5638, a novel estrogen ligand, provides insights into the role of estrogen receptor in bone," *Endocrinol.*, 138(9):3901-3911 (1997).
Wu, "Analysing gene expression data from DNA microarrays to identify candidate genes," *J. Pathol.*, 195:53-65 (2001).
Xiong et al., "Biomarker identification by feature wrappers," *Genome Res.*, 11:1878-1887 (2001).
Yamamoto et al., "Differential involvement of the hypermethylator phenotype in hereditary and sporadic colorectal cancers with high-frequency microsatellite instability," *Genes, Chromosomes & Cancer*, 33:322-325 (2002).
Yamamoto et al., "Overexpression of BUBR1 is associated with chromosomal instability in bladder cancer," *Cancer Genet. Cytogenet.*, 174(1):42-47 (2007).
Yang et al., "Normalization for cDNA microarray data: a robust composite method addressing single and multiple slide systematic variation," *Nucleic Acids Res.*, 30(4):e15 (2002).
Yeang et al., "Molecular classification of multiple tumor types," *Bioinformatics*, 17(Suppl. 1):S316-S322 (2001).
Yuan et al., "Increase expression of mitotic checkpoint genes in breast cancer cells with chromosomal instability," *Clin. Cancer Res.*, 12(2):405-410 (2006).
Zhou et al., "A novel transcription factor, ELF5, belongs to the ELF subfamily of ETS genes and maps to human chromosome 11p13-15, a region subject to LOH and rearrangement in human carcinoma cell lines," *Oncogene*, 17(21):2719-2732 (1998).
Zhou et al., "Overexpression of transfected human ribonucleotide reductase M2 subunit in human cancer cells enhances their invasive potential," *Clin. Exp. Metastasis*, 16(1):43-49 (1998).
Zhou et al., "Tumour amplified kinase STK15/BTAK induces centrosome amplification, aneuploidy and transformation," *Nat. Genet.*, 20(2):189-193 (1998).
Zuncai et al., "The prognostic biomarkers HOXB13, IL17BR, and CHDH are regulated by estrogen in breast cancer," *Clin. Cancer Res.*, 13(21):6327-6334 (2007).
Zhang et al., "Breast cancer index identifies early-stage estrogen receptor-positive breast cancer patients at risk for early- and late-distant recurrence," *Clin. Cancer Res.*, 19:4196-4205 (2013).

| Variable* | Univariate HR [95% CI] | P value | Multivariate HR [95% CI] | P value |
|---|---|---|---|---|
| Overall 15-year (n=399) | | | | |
| Age | 0.82 [0.67-1.00] | 0.05 | 0.93 [0.74-1.16] | 0.50 |
| Tumor type | 0.59 [0.35-1.00] | 0.05 | 0.68 [0.39-1.18] | 0.17 |
| Surgery type | 1.75 [1.15-2.66] | 0.01 | 1.41 [0.91-2.18] | 0.13 |
| PR | 0.40 [0.23-0.70] | 0.001 | 0.60 [0.34-1.08] | 0.09 |
| Chemotherapy | 2.25 [1.09-4.66] | 0.03 | 1.60 [0.70-3.63] | 0.26 |
| BCIN+ | 2.14 [1.56-2.94] | <0.0001 | 1.81 [1.36-2.41] | <0.0001 |
| Post-5-year (n=347) | | | | |
| Age | 1.15 [0.85-1.55] | 0.37 | 1.25 [0.88-1.78] | 0.21 |
| Tumor type | 0.35 [0.17-0.72] | 0.005 | 0.40 [0.19-0.85] | 0.017 |
| Surgery type | 1.80 [0.95-3.41] | 0.07 | 1.48 [0.76-2.87] | 0.25 |
| PR | 0.52 [0.20-1.33] | 0.17 | 0.55 [0.21-1.47] | 0.23 |
| Chemotherapy | 1.44 [0.56-3.71] | 0.45 | 1.67 [0.56-4.99] | 0.36 |
| BCIN+ | 1.66 [1.15-2.38] | 0.006 | 1.51 [1.09-2.10] | 0.013 |

FIG. 7

INTEGRATION OF TUMOR CHARACTERISTICS WITH BREAST CANCER INDEX

CROSS-REFERENCE

This application is a divisional of U.S. patent application Ser. No. 15/349,915, filed Nov. 11, 2016, which claims the benefit of priority to U.S. Provisional Application No. 62/255,260, filed Nov. 13, 2015, and U.S. Provisional Application No. 62/265,964, filed Dec. 10, 2015, all of which are incorporated herein by reference in their entireties.

BACKGROUND OF THE INVENTION

Estrogen-receptor-positive breast cancer is a disease with a protracted risk of recurrence. After 5 years of adjuvant tamoxifen, patients have a sustained risk of disease recurrence and death for at least 15 years after diagnosis. Long-term follow-up from pivotal upfront trials of adjuvant aromatase inhibitors, including the Arimidex, Tamoxifen, Alone or in Combination (ATAC) trial and Breast International Group (BIG) 1-98 study (Cuzick et al., 2010), show a continuing rate of recurrence of about 2% per year after initial therapy, with greater than half of all recurrences occurring after 5 years of adjuvant endocrine therapy.

BRIEF SUMMARY OF THE INVENTION

In view of the foregoing, there is a need for extended adjuvant therapy and a biomarker that can guide the treatment decision-making process. The present disclosure generally relates to determination of risk of recurrence and response to treatment in breast cancer, including improved methods for making those determinations.

The inventors have discovered that a Molecular Grade Index (MGI) and Breast Cancer Index (BCI) can achieve more accurate predictions of risk of recurrence and response to treatments by including tumor size and/or tumor grade characteristics into those determinations. These assays are called MGIN+ and BCIN+, respectively.

The present disclosure provides a method of determining risk of recurrence of a breast cancer of a subject is provided. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  determining tumor size and/or grade of the subject's breast cancer;
  combining the subject's MGI index with the tumor size and/or grade to obtain the subject's MGIN+ score;
  establishing an MGIN+ score cut point below which there is no risk of recurrence, determined from MGIN+ indices of a training set of samples of breast cancer tissue in a representative dataset from patients that had breast cancer recurrence and did not have breast cancer recurrence; and
  comparing the subject's MGIN+ score with the cut point. In some embodiments, the cancer of the subject has a low risk of recurrence if the subject's MGIN+ score is below the cut point, and the cancer of the subject has a high risk of recurrence if the subject's MGIN+ score is above the cut point.

Also provided is a method of predicting responsiveness to a therapy of a breast cancer of a subject. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  determining tumor size and/or grade of the subject's breast cancer;
  combining the subject's MGI index with the tumor size and/or grade to obtain the subject's MGIN+ score;
  establishing an MGIN+ score cut point below which the likelihood of responsiveness is below a set level, wherein the MGIN+ score cut point is determined from MGIN+ indices of a training set of samples of breast cancer tissue in a representative dataset from patients that were responsive to the therapy and were not responsive to the therapy;
  comparing the subject's MGIN+ score with the cut point. In some embodiments, the cancer of the subject is not likely to be responsive to the therapy if the subject's MGIN+ score is below the cut point, and the cancer of the subject is likely to be responsive to the therapy if the subject's MGIN+ score is above the cut point.

Additionally provided is a method of determining risk of recurrence of a breast cancer of a subject. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  assaying the sample of breast cancer cells from the subject for the expression levels of HOXB13 and IL17BR;
  calculating the ratio of the expression levels of HOXB13/IL17BR to obtain the subject's H/I ratio;
  summing the subject's H/I ratio with the subject's MGI index to obtain a subject's BCI index;
  determining tumor size and/or grade of the subject's breast cancer;
  combining the subject's BCI index with the tumor size and/or grade to obtain the subject's BCIN+ score;
  establishing a BCIN+ score cut point below which there is no risk of recurrence, wherein the BCIN+ score cut point is determined from BCIN+ indices of a training set of samples of breast cancer tissue in a representative dataset from patients that had breast cancer recurrence and did not have breast cancer recurrence; and
  comparing the subject's BCIN+ score with the cut point. In some embodiments, the cancer of the subject has a low risk of recurrence if the subject's BCIN+ score is below the cut point, and the cancer of the subject has a high risk of recurrence if the subject's BCIN+ score is above the cut point.

Further, a method of predicting responsiveness to a therapy of a breast cancer of a subject is provided. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  assaying the sample of breast cancer cells from the subject for the expression levels of HOXB13 and IL17BR;
  calculating the ratio of the expression levels of HOXB13/IL17BR to obtain the subject's H/I ratio;

summing the subject's H/I ratio with the subject's MGI index to obtain a subject's BCI index;

determining tumor size and/or grade of the subject's breast cancer;

combining the subject's BCI index with the tumor size and/or grade to obtain the subject's BCIN+ score;

establishing a BCIN+ score cut point below which the likelihood of responsiveness is below a set level, wherein the BCIN+ score cut point is determined from BCIN+ indices of a training set of samples of breast cancer tissue in a representative dataset from patients that were responsive to the therapy and were not responsive to the therapy; and comparing the subject's BCIN+ score with the cut point. In some embodiments, the cancer of the subject is not likely to be responsive to the therapy if the subject's BCIN+ score is below the cut point, and the cancer of the subject is likely to be responsive to the therapy if the subject's BCIN+ score is above the cut point.

The inventors have also discovered that MGI and BCI are effective in predicting risk of recurrence and responsiveness to treatment in subjects with lymph node positive breast cancer.

Thus, in some embodiments, a method of determining risk of recurrence of a breast cancer of a subject is provided. In some embodiments, the subject's breast cancer is lymph node positive. In some embodiments, the method comprises:

assaying a sample of breast cancer cells from the subject for the expression levels of BUB1B, CENPA, NEK2, RACGAP1 and RRM2;

combining the expression levels as a single index into a subject's MGI index;

assaying the sample of breast cancer cells from the subject for the expression levels of HOXB13 and IL17BR;

calculating the ratio of the expression levels of HOXB13/IL17BR to obtain the subject's H/I ratio;

summing the subject's H/I ratio with the subject's MGI index to obtain a subject's BCI index;

establishing a BCI score cut point below which there is no risk of recurrence, determined from BCI indexes of a of a training set of samples of breast cancer tissue in a representative dataset from patients that had breast cancer recurrence and did not have breast cancer recurrence; and comparing the subject's BCI score with the cut point; wherein the cancer of the subject has a low risk of recurrence if the subject's BCI score is below the cut point, and the cancer of the subject has a high risk of recurrence if the subject's BCI score is above the cut point.

In some embodiments, the present disclosure provides a method of predicting responsiveness to a therapy of a breast cancer of a subject. In some embodiments, the subject's breast cancer is lymph node positive. In some embodiments, the method comprises:

assaying a sample of breast cancer cells from the subject for the expression levels of BUB1B, CENPA, NEK2, RACGAP1 and RRM2;

combining the expression levels as a single index into a subject's MGI index;

assaying the sample of breast cancer cells from the subject for the expression levels of HOXB13 and IL17BR;

calculating the ratio of the expression levels of HOXB13/IL17BR to obtain the subject's H/I ratio;

summing the subject's H/I ratio with the subject's MGI index to obtain a subject's BCI index;

establishing an BCI score cut point below which the likelihood of responsiveness is below a set level, determined from BCI indexes of a of a training set of samples of breast cancer tissue in a representative dataset from patients whose breast cancer was responsive to the therapy and patients whose breast cancer was not responsive to the therapy; and comparing the subject's BCI score with the cut point. In some embodiments, the cancer of the subject is not likely to be responsive to the therapy if the subject's BCI score is below the cut point, and the cancer of the subject is likely to be responsive to the therapy if the subject's BCI score is above the cut point.

In some embodiments, a method of recommending treatment for a subject that has breast cancer is provided. In some embodiments, the method comprises determining risk of recurrence by one of the above methods, then, if the subject has a low risk of recurrence, recommending no treatment, or if the subject has a high risk of recurrence, (a) recommending treatment with paclitaxel with 5-fluorouracil, doxorubicin and cyclophosphamide if the subject has not previously been treated for breast cancer, or (b) recommending endocrine therapy if the subject has previously been treated for breast cancer.

In some embodiments, a method or treating a subject that has breast cancer that has not been treated is provided. In some embodiments, the method comprises determining risk of recurrence by one of the above-described methods, then, if the subject has a low risk of recurrence, not treating the subject, or if the subject has a high risk of recurrence, treating the subject with paclitaxel with 5-fluorouracil, doxorubicin and cyclophosphamide.

Additionally provided is a method of recommending treatment for a subject that has breast cancer and has previously had chemotherapy, the method comprising predicting responsiveness to endocrine therapy by one of the above-described methods, and recommending treatment of the subject with endocrine therapy if responsiveness is predicted, or recommending discontinuation of endocrine therapy if responsiveness is not predicted.

Also provided is a method of treating a subject that has breast cancer, the method comprising predicting responsiveness to endocrine therapy by one of the above-described methods, and treating the subject with endocrine therapy if responsiveness is predicted, or discontinuing endocrine therapy if responsiveness is not predicted.

Further provided is a method or treating a subject that has breast cancer and has previously had chemotherapy. In some embodiments, the method comprises determining risk of recurrence by one of the above-described methods, then, if the subject has a low risk of recurrence, the subject is not treated, or if the subject has a high risk of recurrence, the subject is treated with endocrine therapy.

BRIEF DESCRIPTION OF THE DRAWINGS

FIG. 7 illustrates example results for univariate and multivariate Cox regression analyses of overall 15-year and post-5-year prognostic performance of BCIN+, in accordance with some embodiments.

DETAILED DESCRIPTION OF THE INVENTION

Figure 1:
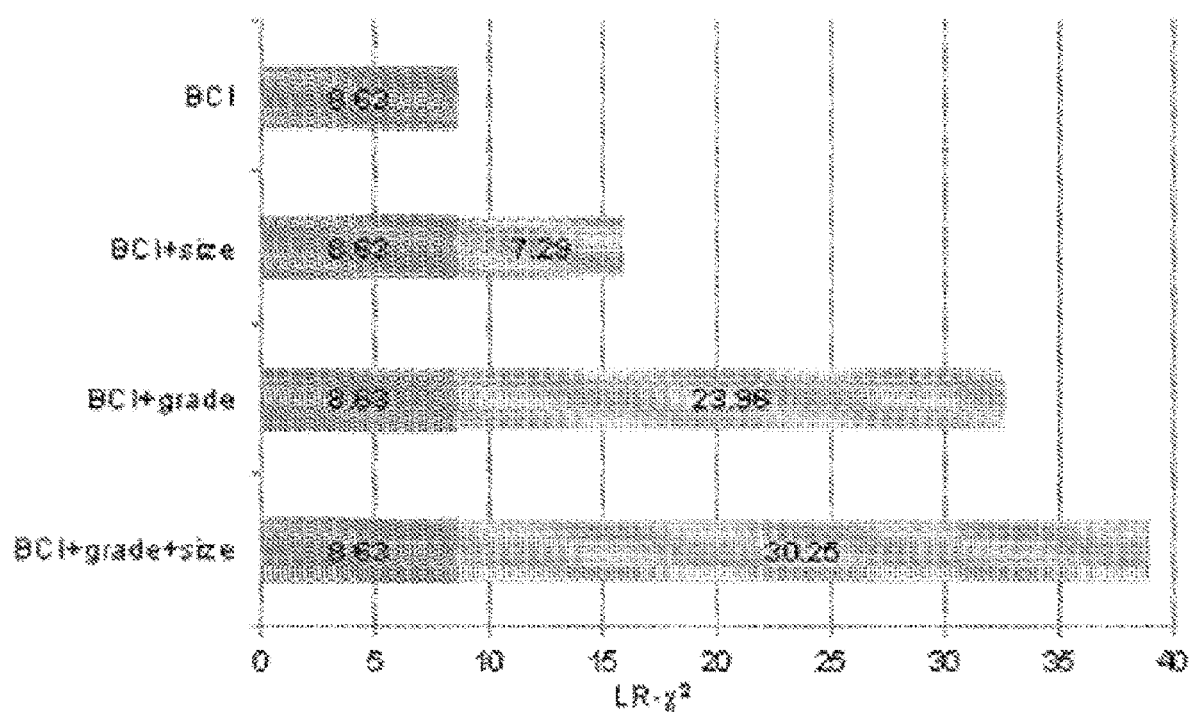
FIG. 1 is a graph showing example prognostic information (LR-$\chi$2) for BCI and additional performance of clinical variables ($\Delta$LR-$\chi$2), in accordance with some embodiments.

As used herein, the singular forms "a", "an" and "the" are intended to include the plural forms as well, unless the context clearly indicates otherwise. Additionally, the use of "or" is intended to include "and/or", unless the context clearly indicates otherwise.

A gene expression "pattern" or "profile" or "signature" refers to the relative expression of one or more genes between two or more clinical outcomes, cancer outcomes, cancer recurrence outcomes, and/or survival outcomes, which is correlated with being able to distinguish between said outcomes. In some cases, the outcome is that of breast cancer.

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

The terms "correlate" or "correlation" or equivalents thereof refer to an association between expression of one or more genes and a physiologic state of a cell to the exclusion of one or more other state as identified by use of the methods as described herein. A gene may be expressed at a higher or a lower level and still be correlated with one or more cancer state or outcome.

A "polynucleotide" is a polymeric form of nucleotides of any length, either ribonucleotides or deoxyribonucleotides. This term refers to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product that can be made enzymatically with DNA or RNA polymerases, for example using polymerase chain reaction (PCR), as is known in the art. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence.

By corresponding is meant that a nucleic acid molecule shares a substantial amount of sequence identity with another nucleic acid molecule. Substantial amount means at least 90%, 95%, 98%, 99%, or 100% sequence identity, such as can be determined using an alignment algorithm, for example the BLAST algorithm, as described in Altschul et al., J. Mol. Biol. 215:403-410 (1990) (using the published default setting, e.g. parameters w=4, t=17). Methods for amplifying mRNA are generally known in the art, and include reverse transcription PCR (RT-PCR) and those described in U.S. Pat. No. 6,794,141. Another method which may be used is quantitative PCR (or Q-PCR). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Some embodiments of the disclosure relate to the identification of genes that are over- or under-expressed. In some embodiments, methods of the disclosure involve determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive nucleotides of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, or at least or about 400 nucleotides of a gene sequence that is not found in other gene sequences. The term "about" as used in the preceding sentence refers to an increase or decrease of 10% from the stated numerical value. Such polynucleotides may also be referred to as polynucleotide probes that are capable of hybridizing to sequences of the genes, or unique portions thereof, described herein. Preferably, the sequences are those of mRNA encoded by the genes, the corresponding cDNA to such mRNAs, and/or amplified versions of such sequences. In preferred embodiments of the disclosure, the polynucleotide probes are immobilized on an array, other devices, or in individual spots that localize the probes.

In some embodiments of the disclosure, all or part of a disclosed sequence may be amplified and detected by methods such as the polymerase chain reaction (PCR) and variations thereof, such as, but not limited to, quantitative PCR (Q-PCR), reverse transcription PCR (RT-PCR), and real-time PCR, optionally real-time RT-PCR. Such methods typically utilize one or two primers that are complementary to portions of a disclosed sequence, where the primers are used to prime nucleic acid synthesis. The newly synthesized nucleic acids are optionally labeled and may be detected directly or by hybridization to a polynucleotide of the disclosure. The newly synthesized nucleic acids may be contacted with polynucleotides (containing sequences) of the disclosure under conditions which allow for their hybridization.

In some embodiments of the disclosure, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. Non-limiting examples of labels include compositions detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "cancer tissue sample" or "cancer cell sample" refers to a cell-containing sample of tissue isolated from an individual afflicted with the corresponding cancer. The sample may be from material removed via a surgical procedure, such as a biopsy. Such samples are primary isolates (in contrast to cultured cells) and may be collected by any suitable means recognized in the art. In some embodiments, the "sample" may be collected by a non-invasive method, including, but not limited to, abrasion or fine needle aspiration.

A "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material. The term may also be limited, if so indicated, as referring only to the transcription of nucleic acids.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because some embodiments of the present disclosure are based on a relative level of gene expression, mutations in non-coding regions of genes as disclosed herein may also be assayed in the practice of the disclosure.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Differences in expression of the disclosed sequences between two conditions being evaluated (e.g., high or low risk of recurrence) are defined in the following terms based upon percent or fold changes in expression between the two conditions. Differences between the two conditions may be of 10, 20, 30, 40, 50, 60, 70, 80, 90, 100, 120, 140, 160, 180, or 200%. Fold increases or decreases from one condition to the other condition may be of 1, 1.5, 2, 2.5, 3, 3.5, 4, 4.5, 5, 5.5, 6, 6.5, 7, 7.5, 8, 8.5, 9, 9.5, or 10.

A "selective estrogen receptor modulator" or SERM is an "antiestrogen" agent that in some tissues act like estrogens (agonist) but block estrogen action in other tissues (antagonist). A "selective estrogen receptor downregulators" (or "SERD"s) or "pure" antiestrogens includes agents which block estrogen activity in all tissues. See e.g. Howell et al. (Best Bractice & Res. Clin. Endocrinol. Metab. 18(1):47-66, 2004). Preferred SERMs of the disclosure are those that are antagonists of estrogen in breast tissues and cells, including those of breast cancer. Non-limiting examples of such include TAM, raloxifene, GW5638, and ICI 182,780. The possible mechanisms of action by various SERMs have been reviewed (see for example Jordan et al., 2003, Breast Cancer Res. 5:281-283; Hall et al., 2001, J. Biol. Chem. 276(40): 36869-36872; Dutertre et al. 2000, J. Pharmacol. Exp. Therap. 295(2):431-437; and Wijayaratne et al., 1999, Endocrinology 140(12):5828-5840). Other non-limiting examples of SERMs include triphenylethylenes, such as tamoxifen, GW5638, TAT-59, clomiphene, toremifene, droloxifene, and idoxifene; benzothiophenes, such as arzoxiphene (LY353381 or LY353381-HCl); benzopyrans, such as EM-800; naphthalenes, such as CP-336,156; and ERA-923.

Non-limiting examples of SERD or "pure" antiestrogens include agents such as ICI 182,780 (fulvestrant or faslodex) or the oral analogue SR16243 and ZK 191703 as well as aromatase inhibitors and chemical ovarian ablation agents as described herein.

Other agents encompassed by SERM as used herein include progesterone receptor inhibitors and related drugs, such as progestomimetics like medroxyprogesterone acetate, megace, and RU-486; and peptide based inhibitors of ER action, such as LH-RH analogs (leuprolide, zoladex, [D-Trp6]LH-RH), somatostatin analogs, and LXXLL motif mimics of ER as well as tibolone and resveratrol. As noted above, preferred SERMs of the disclosure are those that are antagonist of estrogen in breast tissues and cells, including those of breast cancer. Non-limiting examples of preferred SERMs include the actual or contemplated metabolites (in vivo) of any SERM, such as, but not limited to, 4-hydroxytamoxifen (metabolite of tamoxifen), EM652 (or SCH 57068 where EM-800 is a prodrug of EM-652), and GW7604 (metabolite of GW5638). See e.g. Willson et al. (1997, Endocrinology 138(9):3901-3911) and Dauvois et al. (1992, Proc. Nat'l. Acad. Sci., USA 89:4037-4041) for discussions of some specific SERMs.

Other SERMs are those that produce the same relevant gene expression profile as tamoxifen or 4-hydroxytamoxifen. One example of means to identify such SERMs is provided by Levenson et al. (2002, Cancer Res. 62:4419-4426).

Unless defined otherwise all technical and scientific terms used herein have the same meaning as commonly understood to one of ordinary skill in the art to which this disclosure belongs.

Risk of recurrence and responsiveness to therapy in breast cancer can be predicted by measuring expression levels of the genes BUB1B, CENPA, NEK2, RACGAP1, RRA12, HOXB13 and IL17BR; combining the expression levels of BUB1B, CENPA, NEK2, RACGAP1 and RRM2 to obtain the subject's Molecular Grade Index (MGI), and combining the subject's MGI with the ratio of the expression levels of HOXB13/IL17BR, to obtain the subject's Breast Cancer Index (BCI). The subject's BCI is then compared to the BCI values from patients with known outcomes from a representative dataset. MGI is highly prognostic in patients with estrogen-receptor-positive breast cancer. HOXB13/IL17BR (H:I ratio) is prognostic for early and late distant recurrences, and is predictive of extended adjuvant aromatase inhibitor benefit in patients with early-stage estrogen-receptor-positive breast cancer. See for example U.S. Pat. Nos. 7,930,105 and 7,504,214; US Patent Publications 2011/0183858, 2011/0136680, 2013/0281502, and 2015/0203921; and PCT Patent Publication WO/2012/079059. In some cases, integration of clinicopathological factors with other molecular scores can show better prognostic performance than the molecular scores alone (see e.g. Dowsett et al., 2010, J. Clin. Oncol. 28:1829-1834; and Filipits et al., 2011, Clin Cancer Res. 17:6012-6020).

The inventors have discovered that, by combining MGI or BCI with tumor clinical data such as tumor size and/or grade, a more accurate prediction of risk of recurrence and responsiveness is possible. Exemplary procedures for combining MGI or BCI with tumor clinical data, to determine an MGIN+ score or BCIN+ score, respectively, are provided herein, such as in the examples.

In some embodiments, a method of determining risk of recurrence of a breast cancer of a subject is provided. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  determining tumor size and/or grade of the subject's breast cancer;
  combining the subject's MGI index with the tumor size and/or grade to obtain the subject's MGIN+ score;
  establishing an MGIN+ score cut point below which there is no risk of recurrence, determined from MGIN+ indices of a training set of samples of breast cancer tissue in a representative dataset from patients that had breast cancer recurrence and did not have breast cancer recurrence; and
  comparing the subject's MGIN+ score with the cut point. In some embodiments, the cancer of the subject has a low risk of recurrence if the subject's MGIN+ score is below the cut point, and the cancer of the subject has a high risk of recurrence if the subject's MGIN+ score is above the cut point.

Also provided is a method of predicting responsiveness to a therapy of a breast cancer of a subject. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  determining tumor size and/or grade of the subject's breast cancer;
  combining the subject's MGI index with the tumor size and/or grade to obtain the subject's MGIN+ score;
  establishing an MGIN+ score cut point below which the likelihood of responsiveness is below a set level, wherein the MGIN+ score cut point is determined from MGIN+ indices of a training set of samples of breast cancer tissue in a representative dataset from patients that were responsive to the therapy and were not responsive to the therapy;
  comparing the subject's MGIN+ score with the cut point. In some embodiments, the cancer of the subject is not likely to be responsive to the therapy if the subject's MGIN+ score is below the cut point, and the cancer of the subject is likely to be responsive to the therapy if the subject's MGIN+ score is above the cut point.

Additionally provided is a method of determining risk of recurrence of a breast cancer of a subject. In some embodiments, the method comprises:
  assaying a sample of breast cancer cells from the subject for the expression levels of BUB1B, CENPA, NEK2, RACGAP1 and RRM2;
  combining the expression levels as a single index into a subject's MGI index;
  assaying the sample of breast cancer cells from the subject for the expression levels of HOXB13 and IL17BR;
  calculating the ratio of the expression levels of HOXB13/IL17BR to obtain the subject's H/I ratio;
  summing the subject's H/I ratio with the subject's MGI index to obtain a subject's BCI index;
  determining tumor size and/or grade of the subject's breast cancer;
  combining the subject's BCI index with the tumor size and/or grade to obtain the subject's BCIN+ score;
  establishing a BCIN+ score cut point below which there is no risk of recurrence, wherein the BCIN+ score cut point is determined from BCIN+ indices of a training set of samples of breast cancer tissue in a representative dataset from patients that had breast cancer recurrence and did not have breast cancer recurrence; and
  comparing the subject's BCIN+ score with the cut point. In some embodiments, the cancer of the subject has a low risk of recurrence if the subject's BCIN+ score is below the cut point, and the cancer of the subject has a high risk of recurrence if the subject's BCIN+ score is above the cut point.

Further, a method of predicting responsiveness to a therapy of a breast cancer of a subject is provided. The method comprises assaying a sample of breast cancer cells from the subject for the expression levels of BUB1B, CENPA, NEK2, RACGAP1 and RRM2;

combining the expression levels as a single index into a subject's MGI index;

assaying the sample of breast cancer cells from the subject for the expression levels of HOXB13 and IL17BR;

calculating the ratio of the expression levels of HOXB13/IL17BR to obtain the subject's H/I ratio;

summing the subject's H/I ratio with the subject's MGI index to obtain a subject's BCI index;

determining tumor size and/or grade of the subject's breast cancer;

combining the subject's BCI index with the tumor size and/or grade to obtain the subject's BCIN+ score;

establishing a BCIN+ score cut point below which the likelihood of responsiveness is below a set level, wherein the BCIN+ score cut point is determined from BCIN+ indices of a training set of samples of breast cancer tissue in a representative dataset from patients that were responsive to the therapy and were not responsive to the therapy; and comparing the subject's BCIN+ score with the cut point. In some embodiments, the cancer of the subject is not likely to be responsive to the therapy if the subject's BCIN+ score is below the cut point, and the cancer of the subject is likely to be responsive to the therapy if the subject's BCIN+ score is above the cut point.

In some of these embodiments, both the tumor size and grade are combined and contribute to the MGIN+ or BCIN+. See e.g. Example 1.

These methods can be utilized with any breast cancer, including estrogen receptor positive (ER+) and estrogen receptor negative (ER−) breast cancer. Additionally, these methods are useful for lymph node negative (LN−) or lymph node positive (LN+) breast cancer. In some embodiments, 1 to 3 lymph nodes are positive (see e.g. Example 1).

Some embodiments of these methods are also useful for a subject that has been treated for breast cancer, e.g., with endocrine or chemotherapy, for any length of time. In some embodiments, the subject has had 5 years of endocrine therapy.

In some embodiments where the subject has been treated with chemotherapy, the chemotherapy comprised treatment with paclitaxel. In some of these embodiments, the chemotherapy also or alternatively comprised treatment with 5-fluorouracil, doxorubicin and cyclophosphamide.

Methods where response to a therapy is predicted are not limited to predicting response to any particular therapy, including any chemotherapy, any endocrine therapy, radiation therapy and surgery. In some embodiments, response to endocrine therapy, for example to tamoxifen or anastrozole, is predicted. In some embodiments, the endocrine therapy is with a selective estrogen receptor modulator (SERM), e.g., tamoxifen. In other embodiments, the endocrine therapy is with a selective estrogen receptor down-regulator (SERD). In some embodiments, the endocrine therapy is with an aromatase inhibitor (AI), e.g., anastrozole, exemestane or letrozole.

In some embodiments, responsiveness to chemotherapy is determined. In some embodiments, responsiveness to treatment with paclitaxel is predicted. Optionally, such chemotherapy further comprises treatment with 5-fluorouracil, doxorubicin and cyclophosphamide.

In some embodiments, responsiveness to radiation therapy is predicted.

Methods for predicting likelihood of recurrence can encompass any recurrence, e.g., distant recurrence or local recurrence.

In some embodiments, the BCIN+ is calculated by assessing the individual responsiveness or risk of cancer recurrence as part of a continuous BCIN+ variable, wherein the individual responsiveness or risk of recurrence increases in a linear relationship with the BCIN+ variable. See e.g. US Patent Publication 2015/0203921.

In some embodiments of the various methods described herein, any appropriate analytical model can be used to combine the subject's MGI gene expression levels as a single index into a subject's index uses coefficients determined from Cox proportional hazards regression, an accelerated failure time model, a parametric survival model, a logistic model, or a linear discriminant analysis. Non-limiting examples of a parametric survival model includes an exponential survival model and a Weibull survival model. In some embodiments, the coefficients are determined from Cox proportional hazard models.

In some embodiments where the method predicts likelihood of recurrence, the method comprises establishing a cut point for low versus high risk groups that ensures the low risk patients will have minimal 10-year residual disease. This can be established by setting the cut point below where any samples in the training set had recurrence. In those embodiments, a larger training set would provide for greater likelihood that no recurrence will occur.

The inventors have also discovered that MGI and BCI are effective in predicting risk of recurrence and responsiveness to treatment in lymph node positive subjects.

In some embodiments, a method of determining risk of recurrence of a breast cancer of a subject is provided. In some embodiments, the subject's breast cancer is lymph node positive. In some embodiments, the methods comprise:

assaying a sample of breast cancer cells from the subject for the expression levels of BUB1B, CENPA, NEK2, RACGAP1 and RRM2;

combining the expression levels as a single index into a subject's MGI index;

assaying the sample of breast cancer cells from the subject for the expression levels of HOXB13 and IL17BR;

calculating the ratio of the expression levels of HOXB13/IL17BR to obtain the subject's H/I ratio;

summing the subject's H/I ratio with the subject's MGI index to obtain a subject's BCI index;

establishing a BCI score cut point below which there is no risk of recurrence, determined from BCI indexes of a of a training set of samples of breast cancer tissue in a representative dataset from patients that had breast cancer recurrence and did not have breast cancer recurrence; and comparing the subject's BCI score with the cut point; wherein the cancer of the subject has a low risk of recurrence if the subject's BCI score is below the cut point, and the cancer of the subject has a high risk of recurrence if the subject's BCI score is above the cut point.

In some embodiments, a method of predicting responsiveness to a therapy of a breast cancer of a subject. In some embodiments, the subject's breast cancer is lymph node positive. In some embodiments, the method comprises:

assaying a sample of breast cancer cells from the subject for the expression levels of BUB1B, CENPA, NEK2, RACGAP1 and RRM2;

combining the expression levels as a single index into a subject's MGI index;

assaying the sample of breast cancer cells from the subject for the expression levels of HOXB13 and IL17BR;

calculating the ratio of the expression levels of HOXB13/IL17BR to obtain the subject's H/I ratio;

summing the subject's H/I ratio with the subject's MGI index to obtain a subject's BCI index;

establishing a BCI score cut point below which the likelihood of responsiveness is below a set level, determined from BCI indexes of a of a training set of samples of breast cancer tissue in a representative dataset from patients whose breast cancer was responsive to the therapy and patients whose breast cancer was not responsive to the therapy; and comparing the subject's BCI score with the cut point. In some embodiments, the cancer of the subject is not likely to be responsive to the therapy if the subject's BCI score is below the cut point, and the cancer of the subject is likely to be responsive to the therapy if the subject's BCI score is above the cut point.

The above discussion of the methods comprising MGIN+ or BCIN+ also applies to these methods.

Methods described herein may be used to aid in the selection of treatment, such as among endocrine therapy, chemotherapy, radiation therapy, surgery or any combination thereof. In some embodiments, the disclosure includes compositions and methods for determining the expression levels of the MGIN+ or BCIN+ genes and the tumor data, or BCI with LN+ subjects, as a predictor of endocrine therapy effectiveness. In some cases, the predictor may be of responsiveness or non-responsiveness to a SERM, such as tamoxifen, or an SERD. This includes cases where assay of a breast cancer cell containing sample from a subject reveals a low MGIN+ or BCIN+, indicating the likelihood of non-responsiveness to tamoxifen. In other cases, the predictor may be of the effectiveness of one form of endocrine therapy over another. This includes determining MGIN+ or BCIN+ as an indicator of greater responsiveness to an aromatase inhibitor (AI) in comparison to tamoxifen or another SERM or an SERD. Non-limiting examples of an AI include non-steroidal inhibitors such as letrozole and anastrozole and irreversible steroidal inhibitors such as exemestane.

In some embodiments, the disclosure provides compositions and methods for the use MGIN+, BCIN+ or BCT as a predictor of chemotherapy treatment outcome. The MGIN+, BCIN+ or BCI determination may be used to predict chemosensitivity, such as to paclitaxel/FAC (paclitaxel followed by 5-fluorouracil, doxorubicin and cyclophosphamide) or taxol or anthracyclin therapy as non-limiting examples. In some embodiments, the disclosure provides determining MGIN+ or BCIN+, where a high MGIN+ or BCIN+ value is an indicator of increased likelihood of a complete pathological response (pCR) to chemotherapy, such as post-operative (post-surgical intervention) treatment with paclitaxel/FAC as a non-limiting example. As a non-limiting example, the detecting may be of expression in a cancer cell from a pre-operative cell containing sample used to diagnose cancer in the subject.

In some embodiments, a method of recommending treatment for a subject that has breast cancer is provided. In some embodiments, the method comprises determining risk of recurrence by one of the above methods, then, if the subject has a low risk of recurrence, recommending no treatment, or if the subject has a high risk of recurrence, (a) recommending treatment with paclitaxel with 5-fluorouracil, doxorubicin and cyclophosphamide if the subject has not previously been treated for breast cancer, or (b) recommending endocrine therapy if the subject has previously been treated for breast cancer. In some of these embodiments, the subject has previously had chemotherapy and endocrine therapy is recommended. These embodiments may further comprise treating the subject with the recommended treatment.

In some embodiments, a method or treating a subject that has breast cancer that has not been treated is provided. In some embodiments, the method comprises determining risk of recurrence by one of the above-described methods, then, if the subject has a low risk of recurrence, not treating the subject, or if the subject has a high risk of recurrence, treating the subject with paclitaxel with 5-fluorouracil, doxorubicin and cyclophosphamide.

Additionally provided is a method of recommending treatment for a subject that has breast cancer and has previously had chemotherapy, the method comprising predicting responsiveness to endocrine therapy by one of the above-described methods, and recommending treatment of the subject with endocrine therapy if responsiveness is predicted, or recommending discontinuation of endocrine therapy if responsiveness is not predicted. Optionally, where responsiveness is not predicted, the subject is treated with (a) surgery and chemotherapy and/or (b) radiation is recommended.

Also provided is a method of treating a subject that has breast cancer, the method comprising predicting responsiveness to endocrine therapy by one of the above-described methods, and treating the subject with endocrine therapy if responsiveness is predicted, or discontinuing endocrine therapy if responsiveness is not predicted. Optionally, where responsiveness is not predicted, the subject is treated with (a) surgery and chemotherapy and/or (b) radiation is recommended.

Further provided is a method or treating a subject that has breast cancer and has previously had chemotherapy. In some embodiments, the method comprises determining risk of recurrence by one of the above methods, then, if the subject has a low risk of recurrence, the subject is not treated, or if the subject has a high risk of recurrence, the subject is treated with endocrine therapy.

To determine the expression levels of genes, any method known in the art may be utilized. In some embodiments, expression based on detection of mRNA which hybridizes to the genes identified and disclosed herein is used. This is readily performed by any mRNA detection or amplification+ detection method known or recognized as equivalent in the art such as, but not limited to, reverse transcription PCR, the methods disclosed in U.S. Pat. No. 6,794,141, and methods to detect the presence, or absence, of RNA stabilizing or destabilizing sequences. In some embodiments, the mRNA is converted into cDNA.

In some embodiments, the ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene in the "transcriptome" (the transcribed fraction of genes in a genome) or the "proteome" (the translated fraction of expressed genes in a genome). Identifying features include, but are not limited to, unique nucleic acid sequences used to encode (DNA), or express (RNA), said gene or epitopes specific to, or activities of, a protein encoded by said gene. In some embodiments, it is sufficient to provide the identity of the gene(s) used to discriminate between cancer outcomes and an appropriate cell containing sample for use in an expression assay. Similarly, the nature of the cell containing sample is not limiting, as fresh tissue, freshly frozen tissue, and fixed tissue, such as formalin-fixed paraffin-embedded (FFPE) tissues, may be used in the disclosed methods.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, exfoliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

Some embodiments use a nucleic acid based assay to determine expression by immobilization of one or more sequences of the genes identified herein on a solid support, including, but not limited to, a solid substrate such as an array or to beads or bead-based technology. Alternatively, solution based expression assays known in the art may also be used.

The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art, e.g., by deletion from the 5' or 3' end of the sequence) that are optionally minimally interrupted (such as by mismatches or inserted non-complementary basepairs) such that hybridization with a DNA or RNA corresponding to the gene(s) is not affected. In some cases, the polynucleotides used are from the 3' end of the gene, such as within about 350, about 300, about 250, about 200, about 150, about 100, or about 50 nucleotides from the polyadenylation signal or polyadenylation site of a gene or expressed sequence.

The skilled person is fully capable of aligning any two or more of the known expressed sequences for each of these genes to identify an area of identity or conserved changes as a region that uniquely identifies each of these genes in comparison to other genes. Furthermore, the skilled person is fully capable of aligning any two or more of the known expressed sequences for each of these genes to identify an area unique to one or more of the of the expressed sequences as a region that uniquely identifies one known expressed sequence relative to at least one other expressed sequence. As a non-limiting example, a unique region may be in a variant of the expressed sequence for one of the known genes such that the region may be used to identify expression of the variant.

The sequences of the same genes have also been identified and characterized from other animal species. Thus the skilled person in the field is clearly aware of how to identify the disclosed genes relative to other animal genes. The skilled person may also optionally compare the known sequences of the disclosed genes from different animal sources to identify conserved regions and sequences unique to these genes relative to other genes.

Polynucleotides containing mutations relative to the sequences of the disclosed genes may also be used so long as the presence of the mutations still allows hybridization to produce a detectable signal. The immobilized gene(s) may be used to determine the state of nucleic acid samples prepared from sample cancer, or breast, cell(s) for which the outcome of the sample's subject (e.g. patient from whom the sample is obtained) is not known or for confirmation of an outcome that is already assigned to the sample's subject. Without limiting the disclosure, such a cell may be from a patient with ER+ breast cancer. The immobilized polynucleotide(s) need only be sufficient to specifically hybridize to the corresponding nucleic acid molecules derived from the sample under suitable conditions.

As will be appreciated by those skilled in the art, some of the corresponding sequences noted above include 3' polyA (or polyT on the complementary strand) stretches that do not contribute to the uniqueness of the disclosed sequences. The disclosure may thus be practiced with sequences lacking the 3' polyA (or polyT) stretches. The uniqueness of the disclosed sequences refers to the portions or entireties of the sequences which are found only in the disclosed gene's nucleic acids, including unique sequences found at the 3' untranslated portion of the genes. Preferred unique sequences for the practice of the disclosure are those which contribute to the consensus sequences for each of the three sets such that the unique sequences will be useful in detecting expression in a variety of individuals rather than being specific for a polymorphism present in some individuals. Alternatively, sequences unique to an individual or a subpopulation may be used. The preferred unique sequences are preferably of the lengths of polynucleotides of the disclosure as discussed herein.

Methods to identify increased RNA stability (resulting in an observation of increased expression) or decreased RNA stability (resulting in an observation of decreased expression) may also be used. These methods include the detection of sequences that increase or decrease the stability of mRNAs containing the genes' sequences.

These methods also include the detection of increased mRNA degradation. In some embodiments of the disclosure, polynucleotides having sequences present in the 3' untranslated and/or non-coding regions of the above disclosed sequences are used to detect expression levels of the gene sequences in cancer, or breast, cells. Such polynucleotides may optionally contain sequences found in the 3' portions of the coding regions of the above disclosed sequences. Polynucleotides containing a combination of sequences from the coding and 3' non-coding regions preferably have the sequences arranged contiguously, with no intervening heterologous sequences.

In some embodiments, methods of the disclosure may be practiced with polynucleotides having sequences present in the 5' untranslated and/or non-coding regions of the gene sequences in cancer, or breast, cells to detect their levels of expression. Such polynucleotides may optionally contain sequences found in the 5' portions of the coding regions. Polynucleotides containing a combination of sequences from the coding and 5' non-coding regions preferably have the sequences arranged contiguously, with no intervening heterologous sequences. The disclosure may also be practiced with sequences present in the coding regions of the disclosed gene sequences.

Non-limiting polynucleotides contain sequences from 3' or 5' untranslated and/or non-coding regions of at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Even more preferred are polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

In some embodiments, sequences from the 3' or 5' end of the above described coding regions as found in polynucleotides of the disclosure are of the same lengths as those described above, except that they would naturally be limited by the length of the coding region. The 3' end of a coding region may include sequences up to the 3' half of the coding region. Conversely, the 5' end of a coding region may include sequences up to the 5' half of the coding region. Of course the above described sequences, or the coding regions and polynucleotides containing portions thereof, may be used in their entireties.

Polynucleotides combining the sequences from a 3' untranslated and/or non-coding region and the associated 3' end of the coding region may be at least or about 100, at least about or 150, at least or about 200, at least or about 250, at least or about 300, at least or about 350, or at least or about 400 consecutive nucleotides. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

In some embodiments of the disclosure, polynucleotides containing deletions of nucleotides from the 5' and/or 3' end of the above disclosed sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the sequences and the need to be able to use the polynucleotides for the detection of expression levels.

Some polynucleotides of the disclosure from the 3' end of the above disclosed sequences include those of primers and optional probes for quantitative PCR. In some embodiments, the primers and probes are those which amplify a region less than about 350, less than about 300, less than about 250, less than about 200, less than about 150, less than about 100, or less than about 50 nucleotides from the from the polyadenylation signal or polyadenylation site of a gene or expressed sequence.

In some embodiments, polynucleotides containing portions of the above disclosed sequences including the 3' end are used. Such polynucleotides can contain at least or about 50, at least or about 100, at least about or 150, at least or about 200, at least or about 250, at least or about 300, at least or about 350, or at least or about 400 consecutive nucleotides from the 3' end of the disclosed sequences.

The disclosure also includes polynucleotides used to detect gene expression in breast cancer cells. The polynucleotides may comprise a shorter polynucleotide consisting of sequences found in the above genes in combination with heterologous sequences not naturally found in combination with the sequences. Non-limiting examples include short sequences from cloning vectors or present in restriction fragments used to prepare labeled probes or primers as described herein.

The requisite level of expression may be that which is identified by the methods described herein for the genes used. Additionally, the assaying may include preparing RNA from the sample, optionally for use in PCR (polymerase chain reaction) or other analytical methodology as described herein. The PCR methodology is optionally RT-PCR (reverse transcription-PCR) or quantitative PCR, such as real-time RT-PCR. Alternatively, the assaying may be conducted by use of an array, such as a microarray, by next-generation sequencing, or by any other method known in the art. Optionally, the sample of cancer cells is dissected from tissue removed or obtained from said subject. As described herein, a variety of sample types may be used, including a formalin fixed paraffin embedded (FFPE) sample as a non-limiting example.

The term "cut point" as used herein indicates the cut-off value above which MGIN+, BCIN+ or BCI is considered a high value and below which those indices are considered a low value.

By way of non-limiting example, the genes for MGIN+, BCIN+ or BCI may be assayed and used to detect expression levels that, when factoring in tumor clinical data, correspond to a value that is "high risk" (which is above the cut point) for MGIN+, BCIN+ or BCI, or to detect expression levels that correspond to a value that is "low risk" (which is at or below the cut point) for MGIN+, BCIN+ or BCI, as disclosed herein. In some cases, the MGIN+, BCIN+ or BCI cut point threshold may be 1. In alternative embodiments, the cutoff may be at or about 2, at or about 3, at or about 4, at or about 5, at or about 6, at or about 7, at or about 8, at or about 9, at or about 10, greater than 10, or any value in between. In some embodiments, the cutoff is greater than 1, 2, 3, 4, 5, 6, 7, 8, or 9. With respect to the HI ratio, its determination may be made as described in Ma et al., Cancer Cell. 2004 June; 5(6):607-16. Also see e.g. Ma et al., Clin Cancer Res 2008; 14(9): 2601-8; and Ma et al., J Clin Oncol 2006; 24(28): 4611-9.

The cut point value can be determined without undue experimentation by using known methods, for example by using training sets, e.g. as described in Example 1. The cut point can be selected to achieve the sensitivity (SE), specificity (SP), positive predictive value (PPV) and negative predictive value (NPV) desired.

For the evaluation of methods of determining risk of recurrence or response to therapy, categorizations can be used to interpret the results of tests in the clinical setting. The diagnostic or prognostic value of a method can be defined by its SE, SP, PPV and NPV. Any test method will produce True Positives (TP), False Negatives (FN), False Positives (FP), and True Negatives (TN). The "sensitivity" of a test is the percentage of all patients with disease present or that do respond who have a positive test or (TP/TP+FN)× 100%. The "specificity" of a test is the percentage of all patients without disease or who do not respond, who have a negative test or (TN/FP+TN)×100%. The "predictive value" or "PV" of a test is a measure (%) of the times that the value (positive or negative) is the true value, i.e., the percent of all positive tests that are true positives is the Positive Predictive Value (PPV) or (TP/TP+FP)×100%. The "negative predictive value" (NPV) is the percentage of patients with a negative test who will not respond or (TN/FN+TN)×100%. Another measure, the "accuracy" or "efficiency" of a test, is the percentage of the times that the test gives the correct answer compared to the total number of tests or (TP+TN/

TP+TN+FP+FN)×100%. The "error rate" calculates from those patients predicted to respond who did not and those patients who responded that were not predicted to respond or (FP+FN/TP+TN+FP+FN)×100%. The overall test "specificity" is a measure of the accuracy of the sensitivity and specificity of a test do not change as the overall likelihood of disease changes in a population, the predictive value does change. The PV changes with a physician's clinical assessment of the presence or absence of disease or presence or absence of clinical response in a given patient.

For any given test, the TP, FN, FP and TN can be determined and adjusted by the skilled artisan without undue experimentation by, e.g., adjusting the cut point value, adjusting the statistical significance (e.g., the P value) for making the clinical determination; adjusting the accuracy of the test procedures, etc.

Using a cut point of 7 as a non-limiting example for MGIN+, BCIN+, or BCI, the disclosed methods provide two possible assay outcomes for a given sample: high risk or responsive MGIN+, BCIN+, or BCI, corresponding to a value above 7, and low risk or nonresponsive MGIN+, BCIN+, or BCI, corresponding to a value below 7. A high risk or responsive MGIN+, BCIN+, or BCI is indicative of a high risk of recurrence of breast cancer, or responsive to a particular therapy, depending on the clinical parameter under examination. A low MGIN+, BCIN+, or BCI is indicative of a low risk of recurrence, or nonresponsive to the therapy under consideration.

In some embodiments, an MGIN+, BCIN+, or BCI intermediate-risk of cancer recurrence may be included.

As a non-limiting example, the cancer cell may be one from a pre-operative histological sample, or biopsy, used to diagnose cancer in the subject. For such a subject with ductal carcinoma in situ (DCIS), the current standard of care is surgery, with breast conserving surgery preferred over a radical mastectomy, to remove the DCIS. This is often followed by post-operative radiotherapy, optionally with endocrine therapy, such as treatment with tamoxifen, a selective estrogen receptor modulator (SERM), a selective estrogen receptor down-regulator (SERD), an aromatase inhibitor (AI) such as letrozole, a targeted therapy such as anti-mTOR therapy (e.g., with Afinitor®) or anti-HER2 therapy (e.g., with Herceptin®) and/or chemotherapy, using any compound known in the art.

In some cases, the disclosed methods may be used to select or eliminate therapies for premenopausal women, or for postmenopausal women, diagnosed with cancer. Premenopausal women include those who are less than about 35 years of age. In these subjects, high MGIN+, BCIN+, or BCI is an indicator of cancer recurrence or response to therapy. The method may include assaying a breast cancer cell containing sample from a subject for expression of these genes. As a non-limiting example, the cell may be one from a pre-operative histological sample used to diagnose cancer in the subject.

The methods may include identifying the premenopausal subject as likely, or unlikely, to experience cancer recurrence, and optionally further include adjusting treatment modalities for the subject to address the expected outcome. As a non-limiting example, determination of a low likelihood of recurrence may be used to confirm the suitability of, or to select, breast conserving therapies, optionally with reduction in post-operative therapies like radiation and/or endocrine therapy or chemotherapy. As another non-limiting example, determination of a high likelihood of recurrence may be used to confirm the suitability of, or to select, radical treatment modalities with inclusion of post-operative therapies, such as radiation and/or endocrine therapy or chemotherapy.

The determination of MGIN+, BCIN+, or BCI may be in any suitable cell containing sample as described herein. Non-limiting examples of cells for use in the disclosure include those freshly isolated from the subject, those frozen after isolation, and those that are fixed and/or embedded, such as formalin fixed, paraffin embedded (FFPE). In most embodiments, the cells are breast cells, such as breast cancer cells.

In some embodiments, MGIN+, BCIN+, or BCI is used to determine risk of cancer recurrence in a breast cancer afflicted patient. Non-limiting examples of late recurrence include after 5 years of treatment with an aromatase inhibitor, targeted therapy or endocrine therapy, such as tamoxifen, but also includes after 4 years, after 3 years, or after 2 years or less time of treatment. Similarly, the MGIN+ or BCIN+ may be used to predict responsiveness to an anti-aromatase therapy, such as anastrozole or letrozole, targeted therapy or anti-estrogen therapy after the above time periods.

In some embodiments, the methods disclosed herein can be advantageously used on a breast cancer cell-containing sample from a subject, such as a DCIS sample, although the methods described herein can be used with any type of breast cancer, including any non-invasive, or invasive breast cancer, such as invasive ductal carcinoma, invasive lobular carcinoma, inflammatory breast cancer, male breast cancer, metastatic breast cancer, recurrent breast cancer, papillary carcinoma, triple-negative breast cancer, Paget's disease of the nipple, sarcoma of the breast, medullary carcinoma, tubular carcinoma, mucinous carcinoma, metaplastic carcinoma, adenocystic carcinoma, phyllodes tumor and angiosarcoma.

In some embodiments, the present disclosure provides systems for performing any of the methods described herein. Systems can comprise one or more modules, each configured to perform one or more steps of a method disclosed herein. In some embodiments, the system comprises one or more computer processors. In some embodiments, the system further comprises a reaction module in communication with the computer processor, wherein the reaction module performs a reaction for measuring gene expression. Processors can be associated with one or more controllers, calculation units, and/or other units of a computer system, or implanted in firmware as desired. If implemented in software, the routines can be stored in any computer readable memory such as in RAM, ROM, flash memory, a magnetic disk, a laser disk, or other storage medium. Software can be delivered to a computing device via any known delivery method including, for example, over a communication channel such as a telephone line, the internet, a wireless connection, etc., or via a transportable medium, such as a computer readable disk, flash drive, etc. The various steps can be implemented as various blocks, operations, tools, modules or techniques which, in turn, can be implemented in hardware, firmware, software, or any combination thereof. When implemented in hardware, some or all of the blocks, operations, techniques, etc. can be implemented in, for example, a custom integrated circuit (IC), an application specific integrated circuit (ASIC), a field programmable logic array (FPGA), a programmable logic array (PLA), etc. In some embodiments, the computer is configured to receive a user request to measure expression levels of one or more genes in a sample. The computer may receive the user request directly (e.g. by way of an input device such as a keyboard, mouse, or touch screen operated by a user entering a user request) or indirectly (e.g. through a wired or wireless connection, including over the internet). Non-limiting examples of users include the subject providing the sample, medical personnel, clinicians, laboratory personnel, insurance company personnel, or others in the health care industry.

In some embodiments, the system generates a report of results obtained in accordance with a method of the present disclosure. The report can be transmitted to a recipient, such as a user. The report can be communicated to a recipient at a local or remote location using any suitable communication medium. For example, the communication medium can be a display, a network connection, a wireless connection, or an internet connection. A report can be transmitted over such networks or connections (or any other suitable means for transmitting information, including but not limited to mailing a printed report) for receipt by a recipient. The recipient can be but is not limited to a subject, a health care provider, a health care manager, or electronic system (e.g. one or more computers, and/or one or more servers). In some embodiments, the system sends the report to a recipient's device, such as a personal computer, phone, tablet, or other device.

Example embodiments are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1: Integration of Tumor Size and Grade with the Breast Cancer Index for the Prediction of Distant Recurrence in HR+ Breast Cancer with 1-3 Positive Lymph Nodes This example describes a gene expression-based assay that combines two independent biomarkers: the HOXB13:IL17BR expression ratio (WI), which interrogates estrogen signaling, and the Molecular Grade Index (MGI), which quantifies tumor proliferation (see e.g. Zhang et al., 2013, Clin Cancer Res 19, 4196-4205). The combination is referred to as a Breast Cancer Index (BCI). MGI utilizes the combined expression of five genes, BUB1B, CENPA, NEK2, RACGAP1 and RRM2. BCI significantly predicted 10 year distant recurrence (DR) beyond the clinicopathological factors in estrogen receptor positive (ER+), lymph node negative (LN−) breast cancer patients in three cohorts (see e.g. Zhang et al., 2013; Sgroi et al., 2013, Lancet Oncol. 14:1067-1076). BCI also was prognostic in lymph node positive (LN+) patients in transATAC and MA.14 (Sgroi et al., 2013). Here, a distinct BCI model that integrates tumor size and grade was evaluated for prediction of DR in women with 1-3 lymph node positive disease.

219 primary tumor samples from hormonal receptor-positive patients with 1-3 positive lymph nodes treated with 5 years of tamoxifen or anastrozole were examined. Women with four or more positive lymph nodes were excluded. BCI was combined with tumor size and grade into a comprehensive risk score, BCIN+. Kaplan-Meier (KM) estimates of 10 year DR and hazard ratios (HR) and 95% confidence intervals (CI) were estimated. Change in likelihood ratio (LR-$\Delta\chi^2$) values were used to measure prognostic information of each variable alone or combined in a new score. New cutpoints for low versus high risk groups for the new model were determined to ensure the low risk patients had minimal 10-year residual disease.

In 219 LN+ patients, BCI alone provided substantial additional prognostic information to tumor size (LR-$\Delta\chi^2$=11.83, P=0.0006) and grade (LR-$\Delta\chi^2$=8.33, P=0.004). Both clinical variables provided additional significant prognostic information to BCI alone (BCI alone: LR-$\Delta\chi^2$=9.59, P=0.0004; T: LR-$\Delta\chi^2$=7.09, P=0.008; G: LR-$\Delta\chi^2$=27.59, P<0.0001). Integration of tumor size and grade with BCI (BCIN+) provided additional highly significant prognostic information compared to BCI alone (Interquartile I1R=3.15 [95% CI: 1.54-6.04]; LR-$\Delta\chi^2$=33.89, P<0.0001). A cut-point for a very low risk group in this LN+ population was determined, and included 55 (25%) women with no DR within 10 years. In contrast, 51 (31.1%) women developed a DR in the high risk group (N=164). 10-year DR risk for those in the high risk group was 35.4% (95% CI 28.0-44.1%).

Integration of tumor size and grade significantly enhanced the prognostic ability of BCI to predict 10 year DR risk in hormonal receptor-positive patients with 1-3 positive nodes. A significant number of patients have been identified to have a very low 10-year risk for DR, who may choose to safely forego unnecessary adjuvant chemotherapy or extended adjuvant endocrine therapy.

This examples describes development of a distinct BCI model that integrates tumor size and grade for 1-3 LN+ postmenopausal women.

Formalin-fixed, paraffin-embedded (FFPE) blocks of primary tumor were collected from HR+ patients in the transATAC cohort for RNA extraction (extraction by Genomic Health Inc.).

Primary analysis: HR-positive, LN+(1-3 nodes only), no chemotherapy, 5 years of tamoxifen or anastrozole alone (N=219).

Primary endpoint was distant recurrence (DR).

Statistical analyses included Cox proportional hazard models, Kaplan-Meier analyses, and Likelihood Ratio (LR) tests.

The following models were fitted for those with assessed grade (N=209):
BCI alone
BCI+tumor size
BCI+grade
BCI+tumor size+grade
New cut-off points were defined for low vs. high risk groups.

TABLE 1

Baseline characteristics for all, well, and moderate/poorly differentiated

|  | LN+ (1-3) (N = 209) | LN+ (1-3) well differentiated (N = 42) | LN+ (1-3) moderate/poorly differentiated (N = 167) |
|---|---|---|---|
| Age (years), median (IQR) | 66.9 (60.0-73.4) | 62.3 (57.6-69.7) | 68.1 (61.1-73.5) |
| BMT (kg/m$^2$), median (IQR) | 26.2 (23.6-29.2) | 24.6 (21.9-28.0) | 26.7 (24.1-29.8) |
| Tumor size (cm), median (IQR) | 2.1 (1.7-2.8) | 2.1 (1.7-2.8) | 2.2 (1.8-3.0) |

TABLE 1-continued

Baseline characteristics for all, well, and moderate/poorly differentiated

|  | LN+ (1-3) (N = 209) | LN+ (1-3) well differentiated (N = 42) | LN+ (1-3) moderate/poorly differentiated (N = 167) |
|---|---|---|---|
| Grade* | | | |
| Well | 42 (20.1%) | 42 (100%) | 124 (74.3%) |
| Moderate | 124 (56.6%) |  | 43 (25.7%) |
| Poor | 43 (19.6%) |  |  |
| Radiotherapy | 157 (71.7%) | 29 (69.1%) | 123 (73.7%) |
| Mastectomy | 121 (55.3%) | 20 (47.6%) | 92 (55.1%) |
| Distant recurrence | 51 (23.3%) | 0 | 51 (30.5%) |

*For 10 tumors grade was not assessable

Age and BMI were significantly different (P=0.03, P=0.01, resp.) between women with well and moderate/poorly differentiated tumors.

All DR were observed in women with 1-3 LN+ and moderate or poorly differentiated tumors (Table 1).

BCI was strongly prognostic in women with 1-3 LN+ disease (LR-$\chi^2$=8.63, P=0.003) (FIG. 1).

Both the addition of tumor size alone ($\Delta$LR-$\chi^2$=7.29, P=0.007) and specifically grade alone ($\Delta$LR-$\chi^2$=23.96, P<0.001) to the BCI improved the prognostic performance significantly.

The addition of both clinicopathological variables to the BCI performed statistically the best compared to BCI alone ($\Delta$LR-$\chi^2$=30.25, P<0.001) (FIG. 1).

Tumor size and grade were integrated into the BCI by use of multivariate Cox-proportional model.

Figure 2:
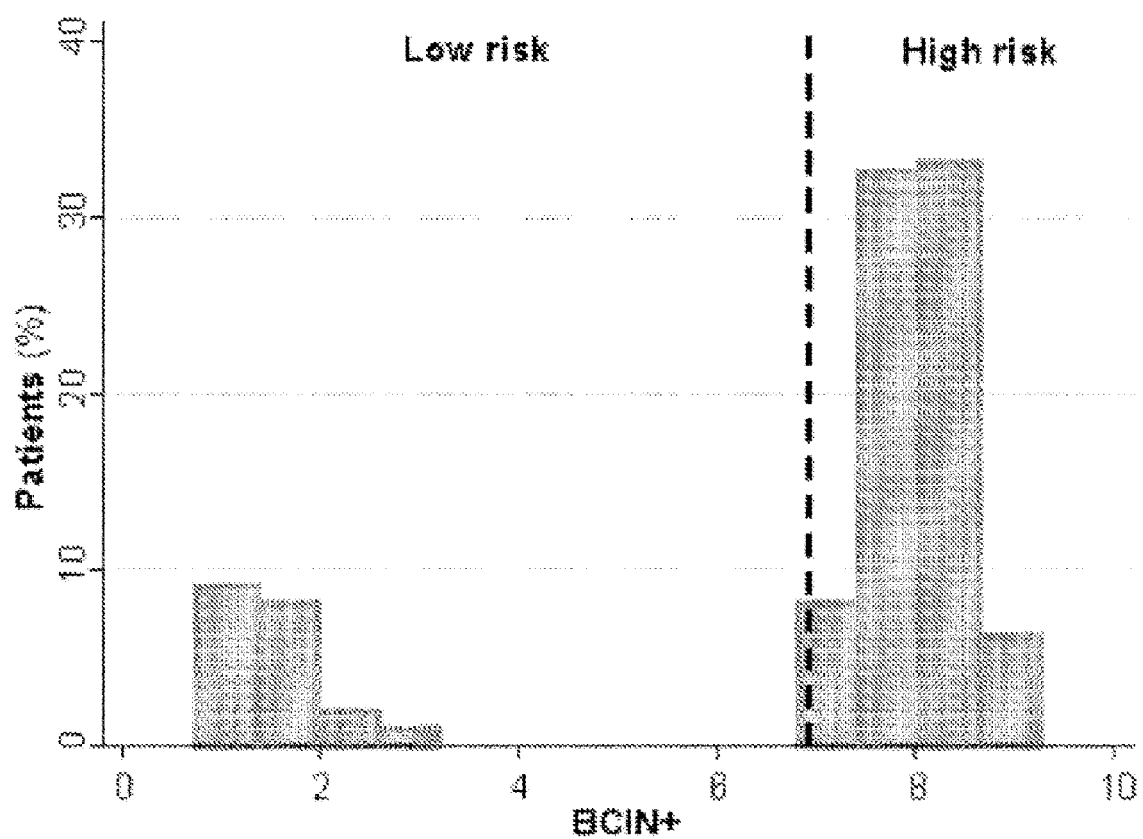
FIG. 2 is a histogram of an example BCIN+ with new defined cut-off point for low versus high risk, in accordance with some embodiments.

A cut-off point for low versus high risk groups was defined (low risk: BCIN+<6.93) that classified around 20% of patients into the low risk group (FIG. 2).

Figure 3:
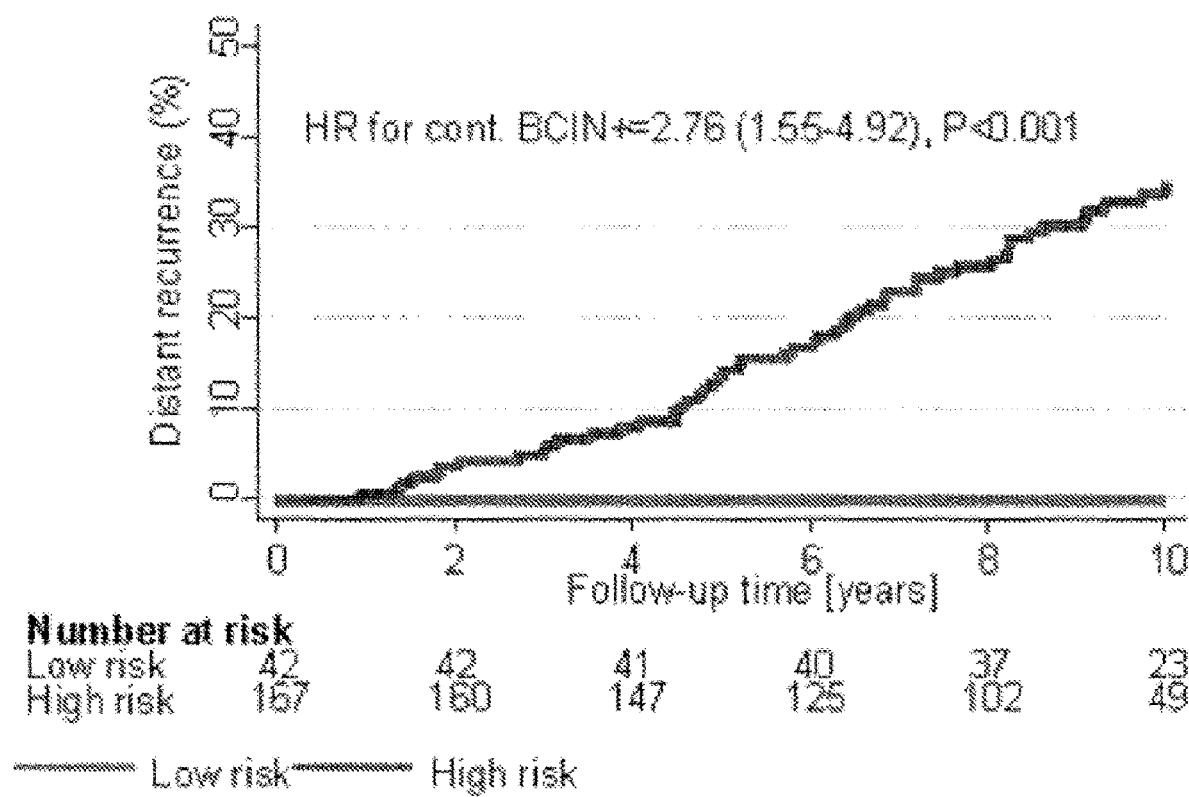
FIG. 3 is a Kaplan-Meier curve and associated HR for example BCIN+ low versus high risk groups, in accordance with some embodiments.

No DR was observed for women categorized into the low risk BCIN+ group. All 51 DR (30.5%) were observed in the high risk BCIN+ group (HR for continuous BCIN+=2.76 (1.55-4.92)) (FIG. 3). The 10-year DR risk for those in the high risk group was 35% (95% CI 27.6%-43.6%).

This BCIN+ model, integrating tumor size and grade, statistically enhanced the prognostic performance of BCI in postmenopausal women with 1-3 LN+ disease.

A significant proportion of women with 1-3 LN+ disease were categorized to have very low risk 10-year DR risk by BCIN+. These women might be spared unnecessary chemotherapy or extended adjuvant endocrine therapy.

Women categorized as BCIN+ high risk had a significantly higher risk of DR (35%) during 10 years of follow-up. These women clearly identified as high risk by BCIN+ may benefit from additional therapy.

Example 2: Validation of BCIN+ Model for Predicting Distant Recurrence in Hormone Receptor-Positive (HR+) Breast Cancer with 1-3 Positive Nodes Women diagnosed with HR+, invasive breast cancer with 1-3 positive nodes (N1 disease) between 1993 and 2007 who received adjuvant endocrine therapy (ET) with or without chemotherapy, at least 5 years of follow-up, and available FFPE tumor blocks were selected for study (N=402). Median follow-up was 12 years. Average patient age was 53 years. Patients included both pre- and post-menopausal women (39%<50 years old; 61%≥50 years old). 81% of patients were treated with adjuvant chemotherapy. All patients were treated with adjuvant ET (TAM=48%; AI=17%; TAM+AI sequence=35%), with 276 treated with up to 5 years of adjuvant ET. Most patients received adjuvant chemotherapy (81%). Most patients had ductal histology (86%). The majority of tumors were T1 (62%) or T2+(35%). 17%, 56%, and 26% of tumors were grade 1, 2, and 3, respectively. Additional baseline characteristics of this study population are provided in Table 2.

TABLE 2

| Characteristic | Category | N (%) |
|---|---|---|
| Age at Surgery | <50 yr | 156 (39%) |
|  | ≥50 yr | 246 (61%) |
| Tumor Size | ≤20 mm | 249 (62%) |
|  | >20 mm | 153 (38%) |
| Tumor Grade | Well | 70 (17%) |
|  | Moderate | 226 (56%) |
|  | Poor | 106 (26%) |
| ER Status | Negative | 4 (1%) |
|  | Positive | 398 (99%) |
| PR Status | Negative | 37 (9%) |
|  | Positive | 364 (91%) |
|  | Unknown | 1 (0%) |
| HER2 Status | Negative | 259 (64%) |
|  | Positive | 52 (13%) |
|  | Unknown | 91 (23%) |
| Surgery | Mastectomy | 162 (40%) |
|  | Lumpectomy | 240 (60%) |
| Tumor Type | Ductal | 347 (86%) |
|  | Lobular | 45 (11%) |
|  | Ductal + Lobular | 10 (3%) |
| Adjuvant Chemotherapy | No | 76 (19%) |
|  | Yes | 324 (81%) |
|  | Unknown | 2 (0%) |
| Adjuvant ET | Tamoxifen (TAM) | 191 (48%) |
|  | Aromatase Inhibitor (AI) | 69 (17%) |
|  | TAM + AI sequence | 142 (35%) |
| Duration of Adjuvant Endocrine Therapy | Initial Adjuvant Only (<5 yr) | 276 (69%) |
|  | Extended (≥5 yr) | 126 (31%) |
| Distant Recurrence | Early (<5 yr) | 49 (56%) |
|  | Late (≥5 yr) | 38 (44%) |
| All Recurrence | Early (<5 yr) | 51 (55%) |
|  | Late (≥5 yr) | 41 (45%) |

Gene expression analyses of formalin-fixed paraffin-embedded (FFPE) samples were performed, while blinded to clinical outcome. For each case, three 10 μm tissue sections were cut, and an H&E slide was used to confirm 40% content of invasive cancer before manual macrodissection to enrich tumor content for RNA extraction. Total RNA was reverse transcribed, the resulting cDNA pre-amplified using the PreAmp Master Mix Kit per manufacturer's instructions (Applied Biosystems, Carlsbad, CA, USA), followed by TaqMan RT-PCR as described by Ma et al., Clin Cancer Res 2008; 14(9): 2601-8. MGI, H/I, and BCI were calculated as described in Ma et al. 2008 and Ma et al., J Clin Oncol 2006; 24(28): 4611-9, blinded to all other variables. The primary endpoint was time to distant recurrence, defined as the time from diagnosis to the time of first metastasis at distant organs. Death before distant recurrence was considered a censoring event. Locoregional recurrences were not considered either as events or as censoring events. Late distant recurrences were defined as distant recurrences occurring after 5 years from diagnosis and were evaluated within the subset of patients who had remained distant recurrence free for at least 5 years.

BCIN+ risk scores and categories ("low" and "high") were determined as in Example 1, including a pre-specified cutpoint, and analyses were blinded to clinical outcomes. Distant recurrence-free survival for the two pre-specified risk groups was evaluated by Kaplan-Meier survival analysis, including estimates of overall (0-15 years) and late (≥5 years) distant recurrence (DR). The equality of the survival curves was evaluated with log-rank test. Multivariate Cox proportional hazard models were used to evaluate whether BCIN+, as a continuous risk index, provided prognostic information. The multivariate analyses were adjusted for age, tumor type, surgery type, PR status, and HER2 status. Patients with missing data on the covariates were excluded from the multivariate analyses. Inter-quartile Hazard ratios (HR) for continuous BCIN+ correspoinding to a change from the 25th to 75th percentile of the distribution, and corresponding 95% confidence intervals (CI) were also calculated. A 2-sided p-value of less than 0.05 was considered statistically significant. All analyses were performed using Stata (version 13.1) or R statistical package (version 3.1.3, www.r-project.org).

Figure 4:
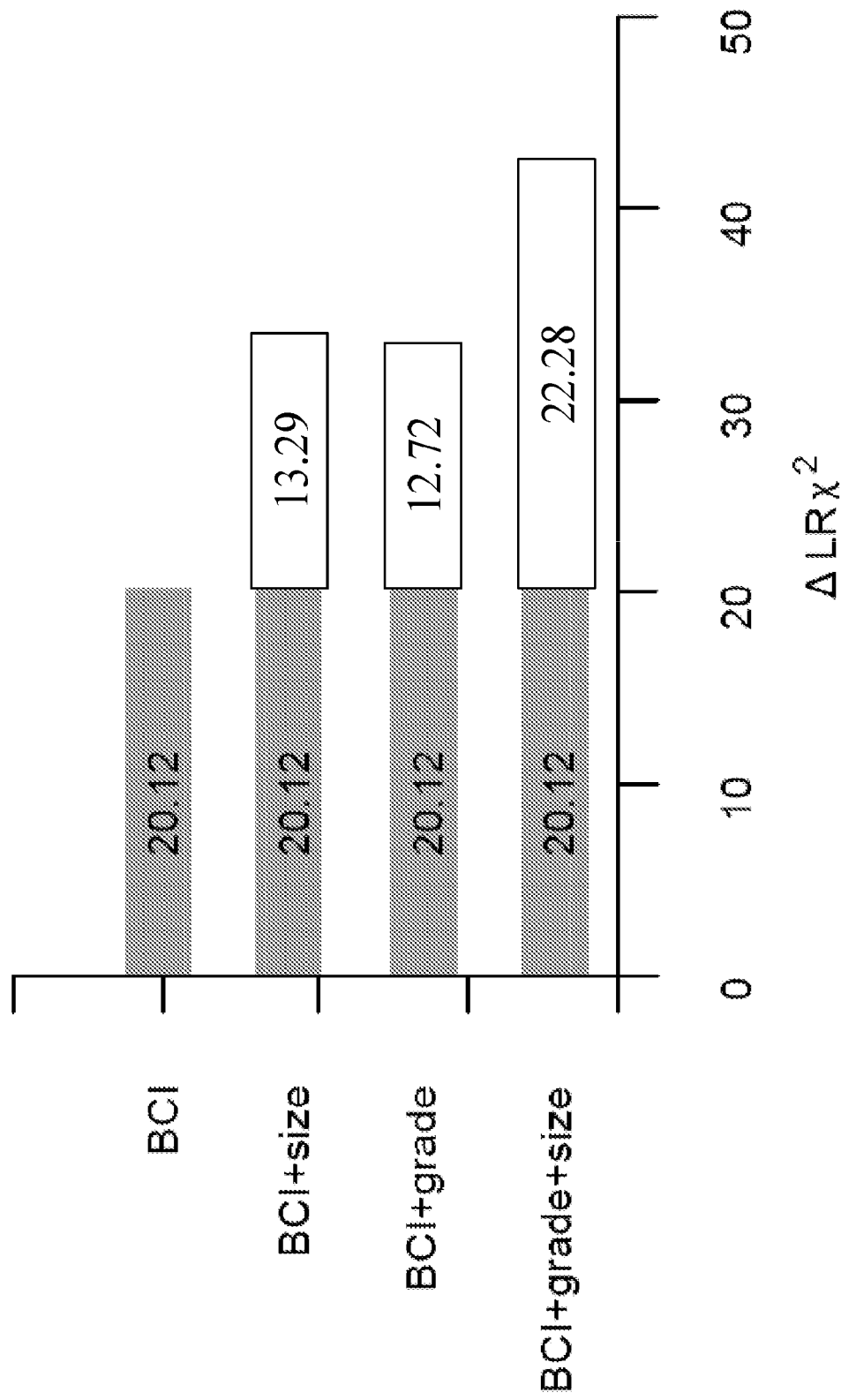
FIG. 4 provides an example illustration of prognostic value of BCI and improvement in the prognostic value by the addition of tumor size, tumor grade, or both, as measured by the change in likelihood ratio statistic, $\chi^2$ ($\Delta LR$-$\chi^2$) in patients with N1 disease, in accordance with some embodiments.

In multivariate analysis, BCIN+ was significantly associated with risk of overall DR (HR 13.1; 95% CI 3.6-43.9; p<0.0001) and late DR (HR 5.0; 95% CI 1.5-16.5; p=0.009). FIG. 4 illustrates prognostic value of BCI and improvement in the prognostic value by the addition of tumor size, tumor grade, or both, as measured by the change in likelihood ratio statistic, $\chi^2$ ($\Delta LR$-$\chi^2$) in patients with N1 disease. The initial value for BCI alone was 20.12 (shaded portion of the bars). The addition of tumor size ($\Delta LR$-$\chi^2$=13.29; P=0.0003), grade ($\Delta LR$-$\chi^2$=12.72; P=0.004), or both tumor size and grade ($\Delta LR$-$\chi^2$=22.28; P=0.0001), in combination with BCI significantly improved the prognostic performance in patients with N1 disease (unshaded portion of the bars).

Figure 5A:
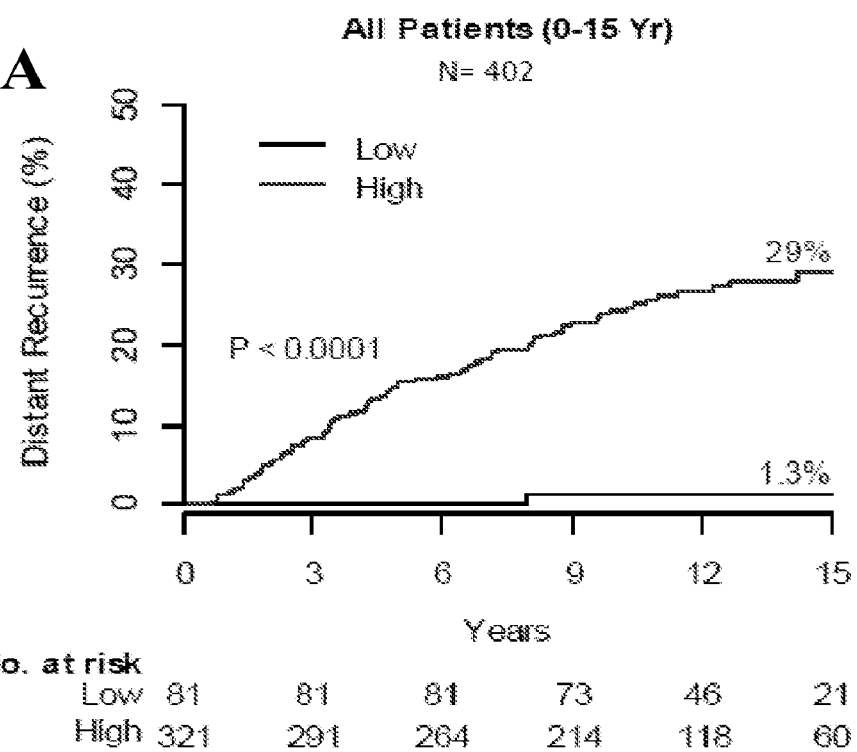
FIGS. 5A-5D illustrates example results for the prognostic performance of BCIN+ for overall 15-year and late post-5-year distant recurrence in patients with N1 disease, in accordance with some embodiments. In each graph, the top line corresponds to distant recurrence in patients classified by BCIN+ as high risk.
Figure 5B:
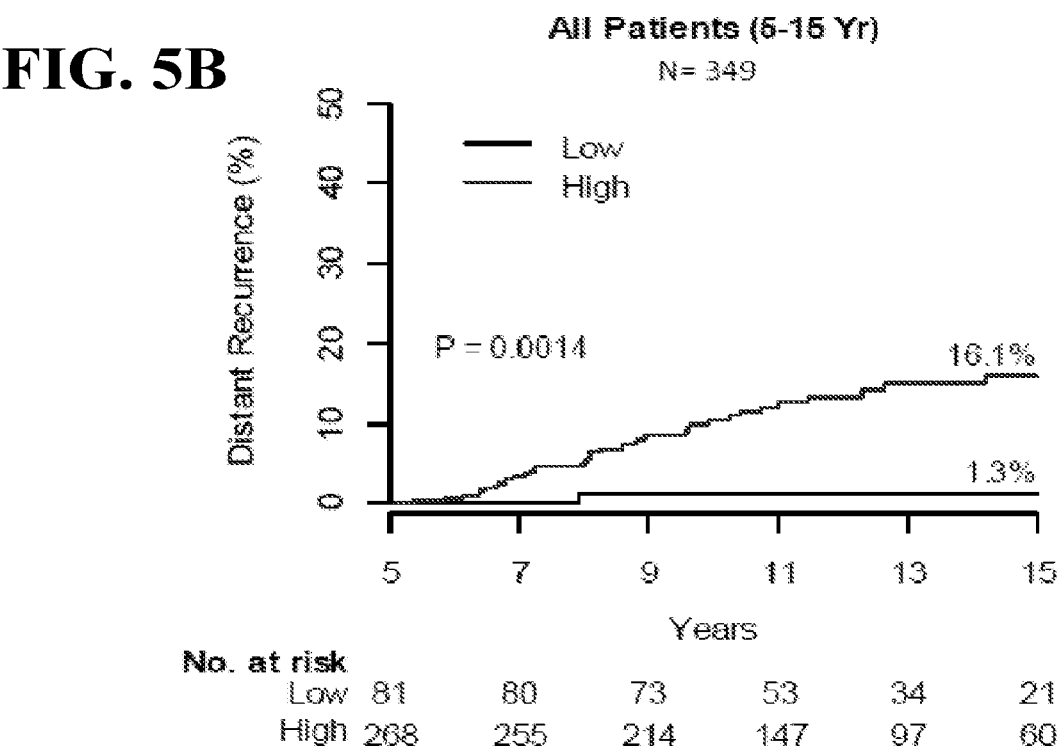
Figure 5C:
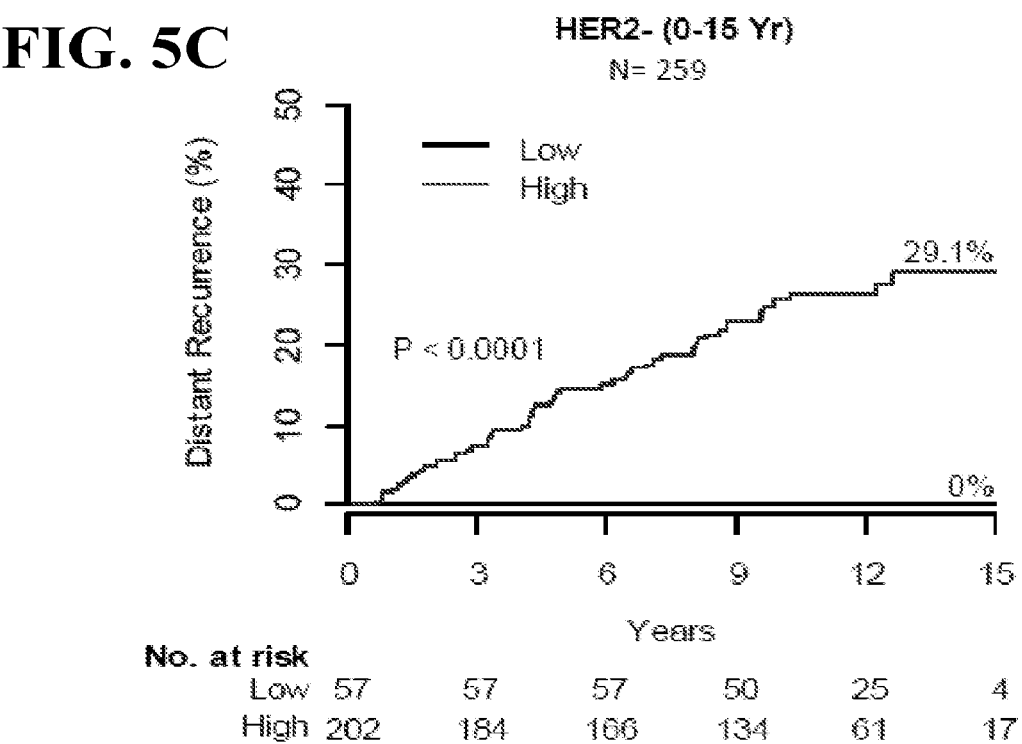
Figure 5D:
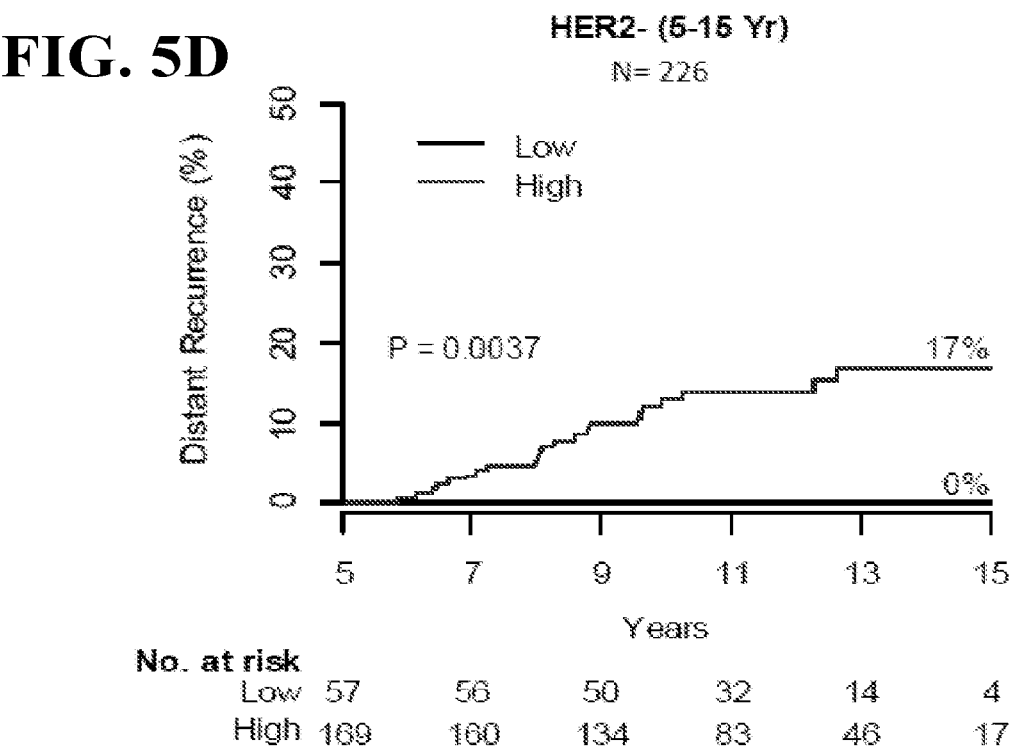

Results for the prognostic performance of BCIN+ for overall 15-year and lat post-5-year distant recurrence in patients with N1 disease are illustrated in FIGS. 5A-5D. For risk of overall cumulative distant recurrence, BCIN+ classified 20% of patients as low risk (N=81), with a 1.3% risk of distant recurrence at both the 10-year and 15-year follow-up (15-year 95% CI 0.0-3.7%); whereas patients classified as BCIN+ high risk had 24.2% risk of distant recurrence at the 10-year follow-up, and a 29% risk of distant recurrence at the 15-year follow-up (15-year 95% CI 23.2-34.4%), giving an HR of 25.93 (95% CI 3.61-186.22) (FIG. 5A). In patients that were distant recurrence-free at year 5 (N=349), BCIN+ classified 23% as low risk, with a 1.3% risk of late distant recurrence at both the 10-year and 15-year follow-up (95% CI 0.0-3.7%); whereas patients classified as BCIN+ high risk had a 10.5% risk of late distant recurrence at the 10-year follow-up, and a 16.1% risk at the 15-year follow-up (95% CI 10.6-21.3%), giving an HR of 12.39 (95% CI 1.7-90.35) (FIG. 5B). Similar results were observed in the HER2-subset for overall 15-year risk of distant recurrence and risk of late (5-15 year) distant recurrence (FIGS. 5C and 5D, respectively). These results indicate that a classification of low risk according to a BCIN+ model carries such a low risk of late recurrence (1.3%) that continued endocrine therapy beyond year 5 is unlikely to substantially reduce that risk of recurrence.

Figure 6:
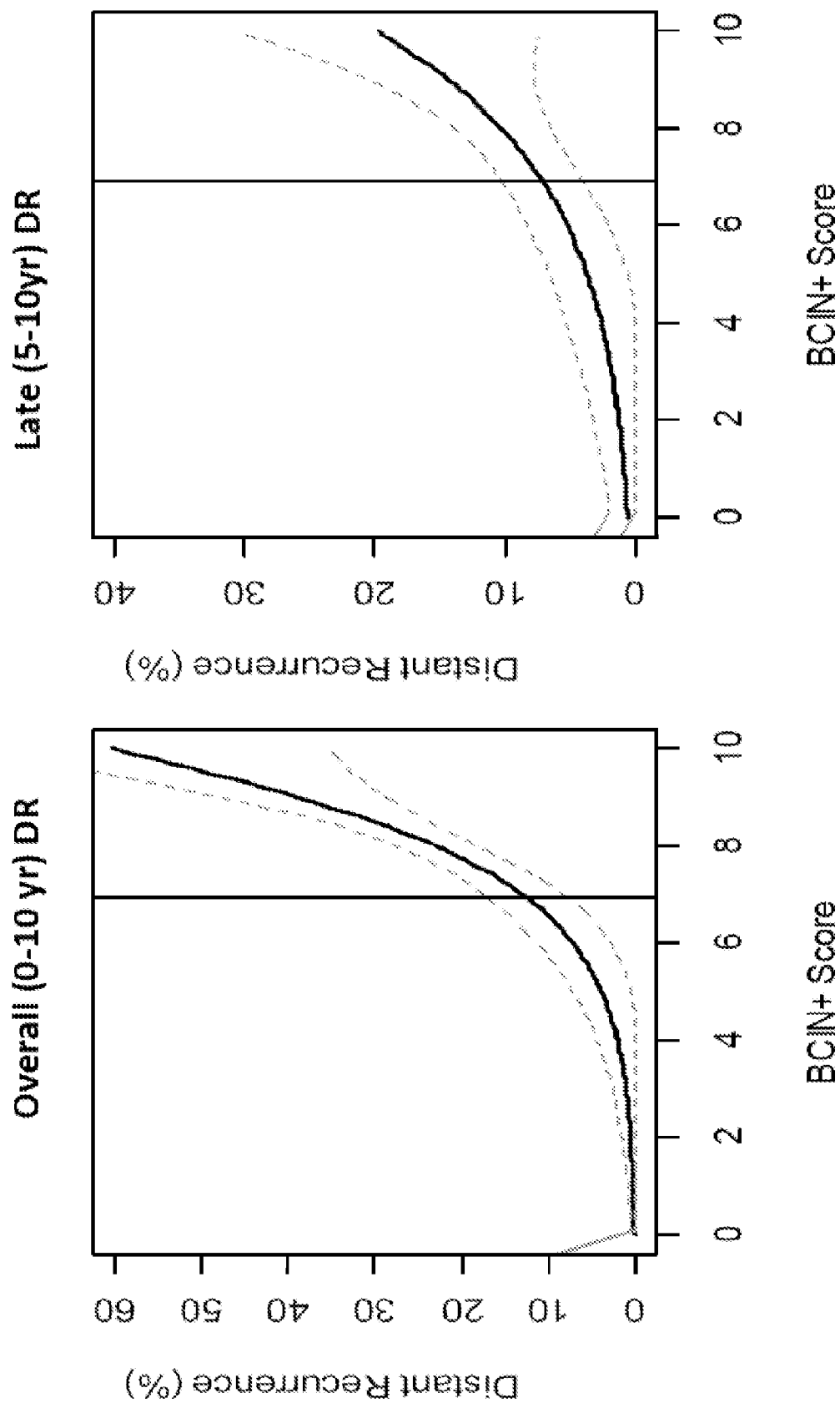
FIG. 6 illustrates example results for the rates of overall (0-10 year) and late (5-10 year) distant recurrence as a function of continuous BCIN+, in accordance with some embodiments.

FIG. 6 illustrates results for the rates of overall (0-10 year) and late (5-10 year) distant recurrence as a function of continuous BCIN+. The plots show that risk of distant recurrence increased monotonically as BCIN+ increased for both overall and late distant recurrence. Results for univariate and multivariate Cox regression analyses of overall 15-year and post-5-year prognostic performance of BCIN+ are provided in FIG. 7. Further with regard to FIG. 7, age was by 10-year increments, tumor type was ductal vs. non-ductal; surgery was mastectomy vs. lumpectomy; PR was positive vs. negative; chemotherapy was yes vs. no; BCIN+ was a continuous variable per inter-quartile range. Patients with missing data on the covariates were excluded from the multivariate analyses. As a continuous variable, BCIN+ was a highly significant prognostic factor with an HR or 2.14 (95% CI 1.56-2.94, P<0.0001) and 1.66 (95% CI 1.15-2.38, P=0.006) for overall and late distant recurrence, respectively.

BCIN+ can provide additional prognostic information to facilitate selection of N+ patients for extended endocrine treatment. In accordance with some embodiments, patients identified as BCIN+ low may be considered adequately treated with adjuvant therapy alone.

Example 3: Subset Analysis of Impact of Treatment History on BCIN+ Prognostic Ability The patient population of Example 2 was analyzed to assess the impact of treatment history on the prognostic ability of a BCIN+ model as in Example 1. BCIN+ risk scores were determined and patients stratified into low risk or high risk categories using a pre-specified cut-point, blinded to clinical outcome. Kaplan-Meier survival analysis was used to estimate overall (0-15 year) and late (5-15 year) distant recurrence (DR), and the difference was evaluated by log-rank test. Treatment-specific subsets were analyzed based on adjuvant endocrine (tamoxifen (TAM)) only versus any history of aromatase inhibitors (AI), and adjuvant chemotherapy treatment history. As explained in Example 2, BCIN+ classified 20% of patients in this population as low risk, and 80% as high risk.

In patients treated with TAM only, BCIN+ low risk and high risk had significantly different 15-year rates of DR of 4.0% (95% CI 0.0-11.4%) versus 41.7% (95% CI 33.0-49.3%), respectively (p=0.0005). For patients disease-free at year 5, rates of late DR (5-15y) were 4.0% (95% CI 0.0-11.5%) versus 20.0% (95% CI 11.4-27.8%), respectively (p=0.04). In patients treated with an AI, BCIN+ low risk and high risk had significantly different 15-year rates of DR of 0% (95% CI 0.0-0.0%) versus 15.0% (95% CI 8.1-21.5%), respectively (p=0.006). For patients disease-free at year 5, rates of late DR were 0.0% (95% CI 0.0-0.0%) versus 12.2% (95% CI 5.6-18.3%), respectively (p=0.02). There was no statistically significant difference in the prognostic performance of BCIN+ between patients treated with TAM only versus those with treatment including any history of AI (interaction p=0.99).

In the subset of patients treated with chemotherapy, BCIN+ classified 19% and 81% of patients as low and high risk with significantly different 15-year rates of DR of 1.7% (95% CI 0.0-4.9%) versus 30.9% (95% CI 24.4-36.8%), respectively (p<0.0001). For patients disease-free at year 5, rates of late DR were 1.7% (95% CI 0.0-4.9%) and 16.3% (95% CI 10.2-21.9%), respectively (p=0.006).

These results demonstrate an ability of BCIN+ to identify a subset of patients with significantly low risk of recurrence across adjuvant endocrine and chemotherapy treatment backgrounds. BCIN+ can provide additional prognostic information to facilitate selection of N+ patients for extended endocrine treatment. In accordance with some embodiments, patients identified as BCIN+ low may be considered adequately treated with adjuvant therapy alone.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating breast cancer of a subject who is lymph node-positive, the method comprising
   (i) determining that the subject has an MGIN+ score above an MGIN+ score cut point by:
   assaying or having assayed a sample of breast cancer cells from the subject for the expression levels of BUB1B, CENPA, NEK2, RACGAP1 and RRM2;
   summing or having summed the expression levels of BUB1B, CENPA, NEK2, RACGAP1 and RRM2 as a single index into a subject's MGI index;
   determining or having determined one or more clinicopathological factor selected from tumor size and grade of the subject's breast cancer;
   calculating or having calculated the MGIN+ score of the subject by combining the subject's MGI index with the one or more clinicopathological factor of the subject using a multivariate Cox-proportional model;
   comparing or having compared the subject's MGIN+ score to the MGIN+ score cut point, wherein the MGIN+ score cut point has been pre-determined based on the MGIN+ scores calculated for a training set of samples containing breast cancer tissues from patients who had breast cancer recurrence and patients who did not have breast cancer recurrence; and
   (ii) treating the subject with an MGIN+ score above the MGIN+ cut point with chemotherapy or endocrine therapy.

2. The method of claim 1, wherein the subject has previously been treated for breast cancer with chemotherapy.

3. The method of claim 1, wherein the subject has previously been treated for breast cancer with five years of endocrine therapy.

4. The method of claim 3, wherein the previous endocrine therapy comprised treatment with tamoxifen or anastrozole.

5. The method of claim 1, wherein the subject is treated with
   (a) endocrine therapy, if the subject has previously been treated for breast cancer, or
   (b) paclitaxel with 5-fluorouracil, doxorubicin and cyclophosphamide, if the subject has not previously been treated for breast cancer.

6. The method of claim 5, wherein the endocrine therapy comprises tamoxifen or anastrozole.

7. The method of claim 1, wherein combining or having combined the subject's expression levels of BUB1B, CENPA, NEK2, RACGAP1 and RRM2 as a single index into the subject's MGI index uses or has used coefficients determined from a Cox proportional hazards regression, an accelerated failure time model, a parametric survival model, a logistic model, or a linear discriminant analysis.

8. The method of claim 7, wherein the coefficients are or have been determined from a Cox proportional hazards regression.

9. The method of claim 1, wherein the patients from the training set with MGIN+ scores below the cut point have minimal 5-year breast cancer recurrence.

10. The method of claim 9, wherein the recurrence is distant recurrence.

11. The method of claim 9, wherein the recurrence is local recurrence.

12. The method of claim 1, wherein the patients from the training set with MGIN+ scores below the cut point have minimal 10-year residual disease.

13. The method of claim 1, wherein 1 to 3 lymph nodes are positive.

14. The method of claim 1, wherein the subject's breast cancer is estrogen receptor positive.

15. A method of treating breast cancer of a subject who is lymph node-positive, the method comprising
    (i) determining that the subject has an MGIN+ score above 7 by:
    assaying or having assayed a sample of breast cancer cells from the subject for the expression levels of BUB1B, CENPA, NEK2, RACGAP1 and RRM2;
    summing or having summed the expression levels of BUB1B, CENPA, NEK2, RACGAP1 and RRM2 as a single index into a subject's MGI index;
    determining or having determined one or more clinicopathological factor selected from tumor size and grade of the subject's breast cancer;
    calculating or having calculated the MGIN+ score of the subject by combining the subject's MGI index with the one or more clinicopathological factor of the subject using a multivariate Cox-proportional model; and
    (ii) treating the subject with an MGIN+ score above 7 with chemotherapy or endocrine therapy.

16. The method of claim 15, wherein the subject is treated with
    (a) endocrine therapy, if the subject has previously been treated for breast cancer, or
    (b) paclitaxel with 5-fluorouracil, doxorubicin and cyclophosphamide, if the subject has not previously been treated for breast cancer.

17. The method of claim 16, wherein the endocrine therapy comprises tamoxifen or anastrozole.

18. A method of treating breast cancer of a subject who is lymph node-positive, the method comprising
    (i) determining that the subject has an MGIN+score above an MGIN+score cut point by:
    assaying or having assayed a sample of breast cancer cells from the subject for the expression levels of BUB1B, CENPA, NEK2, RACGAP1 and RRM2;
    summing or having summed the expression levels of BUB1B, CENPA, NEK2, RACGAP1 and RRM2 as a single index into a subject's MGI index;
    determining or having determined one or more clinicopathological factor selected from tumor size and grade of the subject's breast cancer;

calculating or having calculated the MGIN+ score of the subject by combining the subject's MGI index with the one or more clinicopathological factor of the subject using a multivariate Cox-proportional model;

comparing or having compared the subject's MGIN+ score to the MGIN+ score cut point, wherein the MGIN+ score cut point has been pre-determined based on the MGIN+ scores calculated for a training set of samples containing breast cancer tissues from patients who were responsive to endocrine therapy and patients who were not responsive to endocrine therapy; and (ii) treating the subject with an MGIN+ score above the MGIN+ cut point with endocrine therapy.

19. The method of claim 18, wherein the endocrine therapy comprises tamoxifen or anastrozole.

20. The method of claim 18, wherein the subject's breast cancer is estrogen receptor positive.

\* \* \* \* \*